US008366630B2

(12) United States Patent
Haick et al.

(10) Patent No.: US 8,366,630 B2
(45) Date of Patent: Feb. 5, 2013

(54) CARBON NANOTUBE STRUCTURES IN SENSOR APPARATUSES FOR ANALYZING BIOMARKERS IN BREATH SAMPLES

(75) Inventors: Hossam Haick, Haifa (IL); Peng Gang, Chengsha (CN)

(73) Assignee: Technion Research and Development Foundation Ltd., Haifa (IL)

( * ) Notice: Subject to any disclaimer, the term of this patent is extended or adjusted under 35 U.S.C. 154(b) by 108 days.

(21) Appl. No.: 12/994,177

(22) PCT Filed: May 27, 2009

(86) PCT No.: PCT/IL2009/000532
§ 371 (c)(1),
(2), (4) Date: Nov. 23, 2010

(87) PCT Pub. No.: WO2009/144725
PCT Pub. Date: Dec. 3, 2009

(65) Prior Publication Data
US 2011/0098591 A1 Apr. 28, 2011

Related U.S. Application Data

(60) Provisional application No. 61/056,841, filed on May 29, 2008.

(51) Int. Cl.
*A61B 5/08* (2006.01)
(52) U.S. Cl. ........ 600/532; 600/529; 977/746; 977/748; 977/904; 977/920
(58) Field of Classification Search .................. 600/532, 600/529; 977/746, 748, 904, 920
See application file for complete search history.

(56) References Cited

U.S. PATENT DOCUMENTS

| 6,312,390 B1 * | 11/2001 | Phillips ................. 600/532 |
| 6,411,905 B1 | 6/2002 | Guoliang |
| 6,606,566 B1 | 8/2003 | Sunshine |
| 6,609,068 B2 | 8/2003 | Cranlley |
| 6,620,109 B2 | 9/2003 | Hanson, III |
| 6,767,732 B2 | 7/2004 | Alocilja |
| 6,773,926 B1 | 8/2004 | Freund |
| 6,820,012 B2 | 11/2004 | Sunshine |
| 6,839,636 B1 | 1/2005 | Sunshine |
| 6,841,391 B2 | 1/2005 | Lewis |
| 7,052,854 B2 | 5/2006 | Melker |
| 7,076,371 B2 | 7/2006 | Fu |
| 7,153,272 B2 | 12/2006 | Talton |
| 7,547,931 B2 * | 6/2009 | Star et al. ................ 257/253 |

(Continued)

FOREIGN PATENT DOCUMENTS

| WO | 2008/039165 A1 | 4/2008 |
| WO | 2008/052104 A1 | 5/2008 |

OTHER PUBLICATIONS

Amorim, Leiliane Coelho A. and Cardeal, Zenilda de L. (2007) Breath air analysis and its use as a biomarker in biological monitoring of occupational and environmental exposure to chemical agents. J. Chromatography B 853 (1-2):1-9.

(Continued)

*Primary Examiner* — Patricia Mallari
(74) *Attorney, Agent, or Firm* — Browdy and Neimark, P.L.L.C.

(57) ABSTRACT

The present invention provides a system for measuring biomarker analytes indicative of various diseases comprising an array of sensors sensitive to volatile organic compounds. Particularly, the system is composed of a random network of single-walled carbon nanotubes (SWCNTs) coated with non-polar small organic molecules in conjunction with learning and pattern recognition algorithms. Methods of discriminating between breath samples of healthy individuals and of lung cancer patients are disclosed.

22 Claims, 19 Drawing Sheets

U.S. PATENT DOCUMENTS

| | | | |
|---|---|---|---|
| 2002/0117659 | A1 | 8/2002 | Lieber |
| 2005/0054942 | A1* | 3/2005 | Melker et al. .................. 600/532 |
| 2007/0048180 | A1 | 3/2007 | Gabriel |
| 2007/0106168 | A1* | 5/2007 | O'Neil et al. .................. 600/532 |
| 2008/0021339 | A1* | 1/2008 | Gabriel et al. .................. 600/532 |

OTHER PUBLICATIONS

Aspnes, D. E. and Theeten, J. B. (1980) Spectroscopic Analysis of the Interface Between Si and Its Thermally Grown Oxide. J. Electrochem. Soc. 127(6):1359-1365.

Buszewski, Boguslaw et al., (2007) Human exhaled air analytics: biomarkers of diseases. Biomed. Chromatogr. 21 (6):553-566.

Cao, Wenqing and Duan, Yixiang (2007) Current status of methods and techniques for breath analysis. Crit. Rev. Analy. Chem. 37:3-13.

Chen, Xing et al., (2005) A study of an electronic nose for detection of lung cancer based on a virtual SAW gas sensors array and imaging recognition method. Meas. Sci. Technol. 16(8):1535-1546.

Di Natale, C. et al., (2003) Lung cancer identification by the analysis of breath by means of an array of non-selective gas sensors. Biosens. Bioelectron., 2003, 18(10), 1209-1218.

Dovgolevsky, Ekaterina and Haick, Hossam (2008) Direct observation of the transition point between quasi-spherical and cubic nanoparticles in a two-step seed-mediated growth method. Small 4(11):2059-2066. Epub Oct. 17, 2008.

Gordon, Sydney M. et al., (2002) Volatile organic compounds as breath biomarkers for active and passive smoking. Environ. Health Perspect. 110(7):689-698.

Groves, William A. et al., (1998) Analyzing organic vapors in exhaled breath using a surface acoustic wave sensor array with preconcentration: selection and characterization of the preconcentrator adsorbent. Analy. Chim. Acta. 371:131-143.

Kastler, Marcel et al., (2005) Influence of Alkyl Substituents on the Solution- and Surface-Organization of Hexa-peri-hexabenzocoronenes. J. Am. Chem. Soc. 127(12):4286-4296.

Ouyang, Gangfeng and Pawliszyn, Janusz (2006) SPME in environmental analysis. Anal. Bioanal. Chem. 386 (4):1059-1073.

Parikh, Kunjal et al., (2006) Flexible vapour sensors using single walled carbon nanotubes. Sensors and Actuators B: Chemical 113(1):55-63.

Peng, Gang et al., (2008) Detecting simulated patterns of lung cancer biomarkers by random network of single-walled carbon nanotubes coated with nonpolymeric organic materials. Nano Lett. 8(11):3631-3635.

Peng, Gang et al., (2009) Detection of nonpolar molecules by means of carrier scattering in random networks of carbon nanotubes: toward diagnosis of diseases via breath samples. Nano Lett. 9(4):1362-1368.

Silkoff, P. E. et al., (2005) ATS/ERS Recommendations for Standardized Procedures for the Online and Offline Measurement of Exhaled Lower Respiratory Nitric Oxide and Nasal Nitric Oxide. Am. J. Respir. Crit. Care Med. 171 (8):912-930.

Yu, Hao et al., (2003) Detection volatile organic compounds in breath as markers of lung cancer using a novel electronic nose. Proc. IEEE Sens. 2:1333-1337.

Zhao, Xiao-Mei et al., (1997) Soft lithographic methods for nanofabrication. J. Mater. Chem.7:1069-1074.

Zilberman, Yael et al., (2009) Spong-like structures of hexa-peri-hexabenzocoronenes derivatives enhances the sensitivity of chemiresistive carbon nanotubes to nonpolar volatile organic compounds. Langmuir 25(9):5411-5416.

* cited by examiner

CARBON NANOTUBE STRUCTURES IN SENSOR APPARATUSES FOR ANALYZING BIOMARKERS IN BREATH SAMPLES

REFERENCE TO CO-PENDING APPLICATIONS

Priority is claimed as a U.S. national entry under 35 U.S.C. 371 of PCT/IL2009/000532, filed on May 27, 2009; which claims priority to US provisional patent application Ser. No. 61/056,841, filed on May 29, 2008.

FIELD OF THE INVENTION

The present invention relates to sensor apparatuses comprising single-walled carbon nanotubes for measuring volatile organic compounds. Specifically, the present invention provides methods of using the apparatuses for determining breath analytes indicative of various cancers and, in particular, lung cancer.

BACKGROUND OF THE INVENTION

Breath testing has long been recognized as a reliable technique for diagnosing certain medical conditions through the detection of specific volatile metabolites in exhaled breath (Buszewski et al., Biomed. Chromatogr., 2007, 21, 553-566). The analysis of breath offers several advantages being a non-invasive technique that possess the potential for direct and real-time monitoring (Cao et al., Crit. Rev. Analy. Chem., 2007, 37, 3-13).

Although exhaled breath is mainly composed of $N_2$, $O_2$, $CO_2$, water vapors and other atmospheric constituents (e.g., argon and the like), many volatile compounds which are produced by metabolic processes within the body are found therein. Such metabolic mixtures are relatively less complicated than those obtained from serum or urine samples, and include nitric oxide, nitrogen dioxide, sulfur-conta ining compounds, hydrogen peroxide, carbon monoxide, hydrogen, ammonia, ketones, aldehydes, esters, and alkanes.

Mixtures containing unique compositions of metabolites are indicative of various medical conditions including tissue inflammation (e.g., asthma), immune responses (to cancer cells or bacteria), metabolic disorders (e.g., diabetes), digestive processes, liver and kidney dysfunction, cardiac disorders, gum disease, as well as other physiological conditions. Moreover, mixtures of volatile compounds are characteristic of a certain disease and often display different patterns at different stages of the disease.

Detection of volatile compounds as biomarkers for the diagnosis of medical conditions can be performed using olfactometry systems. These systems, also known as electronic nose devices perform odor detection through the use of an array of cross-reactive sensors in conjunction with pattern recognition algorithms. In contrast to the hitherto "lock-and-key" based devices, wherein each sensor produces an electronic response from a single analyte, in the electronic nose device each sensor is widely responsive to a variety of odorants. In this architecture, each analyte produces a distinct signature from the array of broadly cross-reactive sensors. This configuration allows to considerably widen the variety of compounds to which a given matrix is sensitive, to increase the degree of component identification and, in specific cases, to perform an analysis of individual components in complex multi-component mixtures. Pattern recognition algorithms can then be applied to the entire set of signals, obtained simultaneously from all the sensors in the array, in order to glean information on the identity, properties and concentration of the vapor exposed to the sensor array. Various algorithms and computer controlled systems for olfactometry known in the art are disclosed, for example, in U.S. Pat. Nos. 6,411,905, 6,606,566, 6,609,068, 6,620,109, 6,767,732, 6,820,012, and 6,839,636.

US Patent Application No. 2002/0117659 discloses electrical devices comprised of selectively functionalized nanowires or nanotubes for the detection of analytes.

U.S. Pat. No. 7,153,272 provides methods of collecting and detecting compounds in a human breath sample, comprising a breath collector and a breath analyzer with a plurality of sensors. The methods are directed towards detecting breath compounds for monitoring various medical conditions.

U.S. Pat. No. 7,076,371 discloses methods for characterizing a particular condition or disease from a set of volatile markers which are found, for instance, in the exhaled breath of a person. These markers are detected using a volatile substance detector, such as an artificial olfactory system that includes an artificial neural network/fuzzy filter system equipped with an algorithm for general screening or accurate diagnosis and monitoring, according to need.

U.S. Pat. No. 7,052,854 discloses systems and methods for ex vivo diagnostic analysis of samples of bodily fluids, including exhaled breath. The diagnosis is performed using nanostructure-based assemblies in combination with sensor technology to provide identification of a target analyte/biomarker in a sample.

US Patent Application No. 2007/0048180 discloses a breath analyzer comprising nano-electronic sensors for detecting analytes in human breath. The analyzer contains an integrated multivalent monitor system equipped with a microprocessor capable of analyzing measurements and storing measurement history. The system allows for two or more analytes to be measured in breath samples, and is directed to monitor pulmonary conditions such as asthma.

The analysis of organic vapors in exhaled breath was performed using an array of four polymer-coated surface acoustic wave (SAW) sensors and a thermally desorbable adsorbent pre-concentrator for rapid breath analysis (Groves et al., Analy. Chimi. Acta., 1998, 371, 131-143). The adsorbent used in the pre-concentrator was found critical for achieving adequate sensitivity and further compensate for the high background of water vapors.

Recent studies of gas-chromatography linked to mass-spectrometery (GC-MS) showed that several breath analytes appear to be elevated in instances of lung cancer. Additionally, these analytes are usually detected in distinctive mixture compositions indicative of lung cancer.

Lung cancer was detected by analyzing the breath of patients using a GC column coupled with arrays of polymer-coated surface acoustic wave (Yu et al., Proc. IEEE Sens., 2003, 2, 1333-1337). An artificial neural network has been used, instead of an alveolar gradient, in order to separate the samples into healthy and diseased populations. Using a breath pre-concentrator prior to the GC column, a group of volatile organic compounds characteristic of lung cancer was identified.

In another study, an array of coated quartz crystal microbalance (QCM) sensors was used to detect lung cancer in patients immediately prior to surgical procedure for removing the tumor (Natale et al., Biosens. Bioelectron., 2003, 18(10), 1209-1218). The measurements used the QCM array with no pre-concentration of the breath. The analytes detected by the QCM showed a unique signature.

Recently, sensor arrays of carbon nanotubes coated with different non-polymeric organic layers were shown to be highly potent for the diagnosis of lung cancer via breath samples (Peng et al., *Nano Lett.*, 2008, 8, 3631-3635 and Peng et al., *Nano Lett.*, 2009, 9(4), 1362-1368, published after the priority date of the present application), the contents of which are incorporated by reference herein in their entirety as if fully set forth herein.

In yet another study, carbon nanotubes functionalized with self-assembled sponge like structures of discotic hexa-peri-hexabenzocoronene (HBC) derivatives increased the sensitivity as well as selectivity of the carbon nanotubes to specific VOCs indicative of cancerous breath (Zilberman et al., *Langmuir*, 2009, 25(9), 5411-5416, published after the priority date of the present application), the contents of which is incorporated by reference herein in its entirety as if fully set forth herein.

There still remains an unmet need for apparatuses and methods for detecting minute quantities of analytes released from human breath with high sensitivity. Furthermore, the advantages of these apparatuses and methods would be particularly striking for measuring mixtures of volatile organic compounds indicative of various types of cancers.

SUMMARY OF THE INVENTION

The present invention provides a system comprising an array of sensors for measuring volatile organic compounds as biomarkers for diagnostic and prognostic purposes. In particular, the system of the present invention comprises an array of sensors comprising a (semi-) conductive random network of single-walled carbon nanotubes (SWCNTs) coated with small organic molecules in conjunction with learning and pattern recognition algorithms. The present invention further provides methods of use thereof in measuring breath analytes indicative of cancer, e.g., lung cancer.

The present invention is based in part on the unexpected finding that apparatuses in which the single-walled carbon nanotubes are arranged in networks, display the averaged electrical properties of many randomly distributed SWCNTs. In contrast to apparatuses based on individual SWCNT, in networks of SWCNTs neither position nor structural alignment of the nanotubes is required. Surprisingly, networks of single-walled carbon nanotubes that were coated with small organic molecules produced significantly improved sensing sensitivities in comparison to networks of single-walled carbon nanotubes coated with organic polymers. Additionally, the small organic molecules are essentially non-polar. Unexpectedly, the use of non-polar organic coating provides improved sensitivity as well as selectivity towards VOCs found in the breath of patients having lung cancer.

According to a first aspect, the present invention provides a system for detecting volatile organic compounds derived from a breath sample, the system comprising (a) an apparatus comprising an array of chemically sensitive sensors of single walled carbon nanotubes coated with non-polar small organic molecules; and (b) a processing unit comprising a learning and pattern recognition analyzer wherein the learning and pattern recognition analyzer receives sensor output signals and compares them to stored data.

In one embodiment, the system of the present invention further comprises a breath collector wherein the breath collector comprises at least one of a unit for concentrating breath analytes and a dehumidifying unit.

In another embodiment, the single walled carbon nanotubes coated with non-polar small organic molecules are organized in a random network configuration.

In some embodiments, the network of SWCNTs is fabricated by physical manipulation of the nanotubes. In other embodiments, the network of SWCNTs is fabricated by a self-assembly process.

According to various embodiments, the single-walled carbon nanotubes of the present invention have diameters ranging from about 0.6 nanometer (nm) to about 100 nanometers (nm). More preferably, the single-walled carbon nanotubes have diameters ranging from about 0.7 nm to about 50 nm. Even more preferably, the single-walled carbon nanotubes have diameters ranging from about 0.8 nm to about 10 nm. Most preferably, the single-walled carbon nanotubes of the present invention have diameters ranging from about 0.9 nm to about 5 nm.

In some embodiments, the single-walled carbon nanotubes of the present invention have lengths ranging from about 50 nanometers (nm) to about 10 millimeters (mm). More preferably, the single-walled carbon nanotubes have lengths ranging from about 250 nm to about 1 mm. Even more preferably, the single-walled carbon nanotubes have lengths ranging from about 0.5 micrometer (µm) to about 100 micrometers (µm). Most preferably, the single-walled carbon nanotubes of the present invention have lengths ranging from about 1 µm to about 50 µm.

According to certain embodiments, the surface of the single walled carbon nanotube is functionalized with non-polar small organic molecules, wherein the molecules form thin films having thickness in the range of about 20 nanometers (nm) to about 10,000 nm. In currently preferred embodiments, the surface of the single walled carbon nanotube is functionalized with non-conductive, non-polar small organic molecules.

In various embodiments, the non-polar small organic molecules which are used to functionalize the surface of the single walled carbon nanotubes comprise alkyl, cycloalkyl, alkenyl, alkynyl, aryl, heterocyclyl, heteroaryl, alkylaryl, alkylalkenyl, alkylalkynyl, alkylcycloalkyl, alkylheterocyclyl or alkylheteroaryl functional groups, and combinations and derivatives thereof. Each possibility represents a separate embodiment of the invention.

In further particular embodiments, the non-polar small organic molecules which are used to functionalize the surface of the single walled carbon nanotubes further comprise at least one of a carboxyl, an acyl, an amido, an ester, a cyano, a nitro, an azido, a halogen, a hydroxy, or a haloalkyl moiety. Each possibility represents a separate embodiment of the invention.

In currently preferred embodiments, the non-polar small organic molecules used to functionalize the surface of the nanotubes are selected from the group consisting of propyl gallate, anthracene, tetracosanoic acid, tricosane, 3-methyl-2-phenyl valeric acid, tris(hydroxymethyl)nitro-methane, tetracosane, dioctyl phthalate, 1.2.5.6.9.10-hexabromo-cyclododecane, pentadecane, and combinations and derivatives thereof. Each possibility represents a separate embodiment of the invention.

In additional currently preferred embodiments, the non-polar small organic molecules used to functionalize the surface of the nanotubes are selected from the group consisting of hexa-peri-hexabenzocoronene (HBC) molecules, which are unsubstituted or substituted by any one of 2-ethyl-hexyl (HBC—$C_{6,2}$), 2-hexyldecane (HBC—$C_{10,6}$), 2-decyl tetradecane (HBC—$C_{14,10}$), and dodecane (HBC—$C_{12}$). Each possibility represents a separate embodiment of the invention.

Other suitable non-polar small organic molecules that are within the scope of the present invention include, but are not limited to, the following four main groups of organic compounds, combinations and derivatives thereof:

I) Linear or branched alkanes with $C_1$-$C_{40}$ chain lengths including, but not limited to trioctane, tetradecane, pentadecane, heptadecane, and octadecane.

II) Various sub-groups of alkanes having a substantially similar length with different branching, including, but not limited to dodecane, undecane, tridecane, tetradecane, pentadecane, hexadecane, heptadecane, octadecane, nonadecane, tricosane, docosane, tetracosane, pentacosane, hexacosane, octacosane and nonacosane derivatives such as 2,2-dimethyldodecane, 3-ethyl-3-methyl-undecane, 3-methyltridecane, n-tetradecane, 5-ethyl-5-methyltridecane, 2,2-dimethyltetradecane, 3-ethyl-3-methyltridecane, 3-methylpentadecane, 5-ethyl-5-methylpentadecane, 2,2-dimethylhexadecane, 3-methylheptadecane, 3-ethylheptadecane, 5,5,7,7-tetraethylun-decane, 5-butyl-5-ethyl-tridecane, 5,5-diethylheptadecane, 5-ethylnonadecane, 3,3-dimethylnonadecane, 5,5,11,11-tetraethylpentadecane, 5-butyl-5-ethylheptadecane, 7,7-diethylnonadecane, 6,6-diethyldocosane, 5-ethyl-5-methyltricosane, 2,2-dimethyltetracosane, 3-ethyl-3-methyl-tricosane, 3,3,17,17-tetraethylnonadecane, 5,5-diethyltricosane, 3,3-dimethylpentaco sane, 3,3-diethyltricosane, 6,6-diethyltetracosane, 2,2-dimethylhexacosane, 5-butyl-5-ethyl-tricosane, 3-ethyl-3-methyl-pentacosane, 3,3,19,19-tetraethylhenicosane, 5,5-diethylpentacosane, 3,3-diethylpentacosane, 6,6-diethylhexacosane, 5,5-diethylheptacosane, 6,6-diethyloctacosane, and 5,5-diethylnonacosane.

III) Aromatic compounds having different chain lengths and functionalities including, but not limited to bicycle[4.3.0] nona-3,6(1)-diene, azulene, anthracene, 2,3 benzanthracene, 2,3 benzofluorene, benz[e]-acephenanthrylene, benzo[a]pyrene, and benzo[e]pyrene.

IV) Branched aromatic compounds, including, but not limited to 1,2 benzanthracene, benzo[ghi]perylene, 10-bis (phenylethynyl)anthracene, N,N'-bis(2,5-di-tert-butylphenyl)-3,4,9,10-perylenedi-carboxymide, decacyclene, chrysene, corannulene, phenanthrene, triphenylene, benzo[a]pyrene, coronene, naphthacene, pentacene, pyrene, ovalene, and the like.

Each possibility represents a separate embodiment of the invention.

According to yet another embodiment, the chemically sensitive sensors of single walled carbon nanotubes coated with non-polar small organic molecules of the present invention are configured as any one of the various types of electronic devices, including, but not limited to, capacitive sensors, resistive sensors, impedance sensors, field effect transistor sensors, and the like.

According to certain embodiments, the system of the present invention comprises a processing unit comprising a learning and pattern recognition analyzer, which receives sensor output signals and compares them to stored data. The learning and pattern recognition analyzer utilizes various algorithms including, but not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention. In a currently preferred embodiment, the algorithm used for processing the data is principal component analysis (PCA).

According to a second aspect, the present invention provides a method of determining at least one of the composition and concentration of volatile organic compounds in a breath sample using the system of the present invention, comprising the steps of: (a) providing a system comprising an apparatus comprising an array of chemically sensitive sensors of single walled carbon nanotubes coated with non-polar small organic molecules, and a processing unit comprising a learning and pattern recognition analyzer wherein the learning and pattern recognition analyzer receives sensor output signals from the apparatus and compares them to stored data; (b) exposing the sensor array of the apparatus to the sample; and (c) using pattern recognition algorithms to detect the presence of said volatile compounds in the sample.

In yet another aspect, the present invention provides a method for diagnosing a disease from a breath sample of a subject, comprising: (a) providing a system comprising an apparatus comprising an array of chemically sensitive sensors of single walled carbon nanotubes coated with non-polar small organic molecules, and a processing unit comprising a learning and pattern recognition analyzer wherein the learning and pattern recognition analyzer receives sensor output signals from the apparatus and compares them to stored data, (b) exposing the sensor array of the apparatus to the sample, and (c) using pattern recognition algorithms to detect volatile organic compounds in the sample indicative of a disease in the subject.

In particular embodiments, the detection of volatile organic compounds comprises measuring a change in any one or more of conductivity, resistance, impedance, capacitance, inductance, or optical properties of the sensors upon exposure to VOCs to be detected. In additional embodiments, the detection of volatile organic compounds comprises the use of spectroscopic ellipsometry.

In certain embodiments, the method for diagnosing a disease in a subject presented herein further comprises the step of increasing breath analyte concentrations using a breath collector, wherein the breath collector comprises at least one of a unit for concentrating breath analytes and a dehumidifying unit.

In some embodiments, the system of the present invention provides the detection of a single analyte breath biomarker. In other embodiments, the system of the present invention provides the detection of a plurality of breath biomarkers. In currently preferred embodiments, the system of the present invention provides the detection of non-polar breath biomarkers. In specific embodiments, the system of the present invention provides the detection of breath biomarkers selected from the group consisting of trimethylbenzene, styrene, decane, octane, and 1-hexene.

The medical conditions that can be diagnosed according to the principles of the present invention comprise all indications which are induced due to oxidative stress. According to certain embodiments, the oxidative stress is induced by an oxidizing agent, increased oxygen exposure, oxygen-induced degeneration or disease, reperfusion injury, ionizing radiation, carcinogenic agents, chemotherapeutic agents, mutagenic agents and laser irradiation.

According to particular embodiments, the present invention provides the diagnosis of disorders selected from the group consisting of cancer, arthritis (arthritic conditions), atherosclerosis, kidney diseases, type 2 diabetes, chronic obstructive pulmonary disease (COPD), age related macula degeneration (AMD), neurodegenerative diseases including Alzheimer's disease, Parkinson's disease and amyotrophic lateral sclerosis (ALS). Each possibility represents a separate embodiment of the invention.

According to currently preferred embodiments, the present invention provides the diagnosis of cancers selected from the group consisting of lung cancer, prostate cancer, breast cancer, skin cancer, colon cancer, pancreatic cancer, lymphoma, leukemia, head and neck cancer, kidney cancer, ovarian cancer, bone cancer, liver cancer and thyroid cancer. Each possibility represents a separate embodiment of the invention. In a currently preferred embodiment, the present invention provides the diagnosis of lung cancer in a subject.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
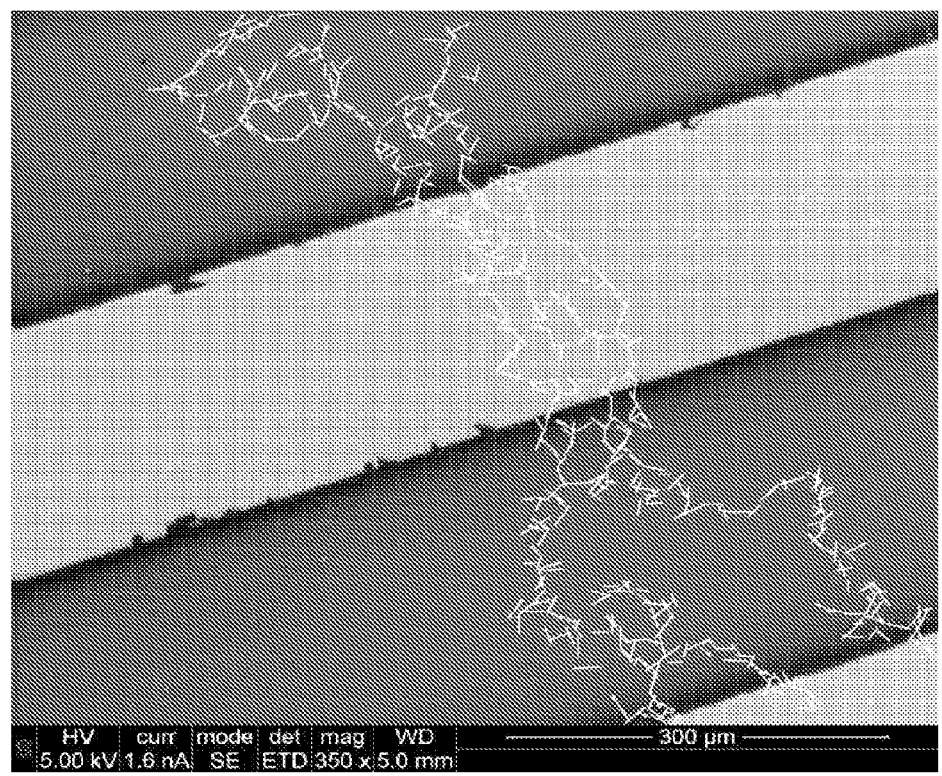
FIG. 1 is a magnified scanning electron micrograph of a random network of SWCNTs contacted by Pd electrodes. White dotted lines were added to highlight the SWCNTs.

The present invention is directed to a system comprising an array of chemically sensitive sensors for measuring breath analytes indicative of various diseases induced by oxidative stress. Particularly, the system comprises a random network of single-walled carbon nanotubes (SWCNTs) coated with non-polymeric organic compounds which are essentially non-polar, in conjunction with learning and pattern recognition analyzer. Methods of discriminating between breath samples of healthy individuals and of cancer patients are disclosed.

The system disclosed herein is based on chemically sensitive vapor detectors comprised of a random network of single-walled carbon nanotubes (SWCNTs) which are coated with non-polar small organic molecules.

Unexpectedly, it has now been found for the first time that sensors of single-walled carbon nanotubes (SWCNTs) coated with non-polymeric, non-polar organic compounds in conjunction with pattern recognition algorithms are capable of differentiating between mixtures of volatile organic compounds which are released from the breath of lung cancer patients and those released from the breath of healthy individuals. In particular, nowhere in the background art was it disclosed or even suggested that a random network of SWCNTs when coated with small organic molecules can provide the detection of breath biomarkers with improved sensitivity to enable the discrimination between healthy and cancerous breath samples. The diversity of functionalities and branching provides discrimination between subtle differences in molecular structures of the analytes to be detected. Such discrimination cannot be obtained using polymeric coatings. The random network geometry provides additional advantages as it eliminates the problems of nanotube alignment and assembly. Furthermore, random configuration eliminates conductivity variations due to nanotube chirality and geometry, and is tolerant to individual SWCNT channel failure since the electronic characteristics of the apparatus are averaged over a large number of nanotubes.

The analysis of breath samples, according to the principles of the present invention, provides the identification of each breath analyte separately, or alternatively the identification of mixtures comprising a plurality of biomarkers. The present invention further provides the reference collection of signatures of biomarker mixtures thus enabling the diagnosis of various medical conditions from breath samples. The use of pattern recognition algorithms further enables post processing of the output signal in order to eliminate extraneous noise. Certain embodiments include multiplexed assays on a single sensor platform or chip. Other embodiments include the diagnosis of lung cancer patient at various stages of the disease.

The present invention provides a system for detecting volatile organic breath analytes, comprising (a) an apparatus comprising an array of chemically sensitive sensors of single walled carbon nanotubes coated with non-polar small organic molecules; and (b) a processing unit comprising an analyzer comprising learning and pattern recognition algorithms.

The system of the present invention may further comprise a breath collector. The breath collector is used to increase sensing sensitivities either by concentrating the breath analytes to be detected or by dehumidifying the patient's breath prior to analyzing. This allows for increased resolution in discriminating between different breath samples.

Breath pre-concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing apparatus for desorption and subsequent analysis (Ouyang, et al., *Anal. Bioanal. Chem.*, 2006, 386, 1059-1073; Coelho et al., *J. Chromatography B*, 2007, 853, 1-9).

Sorbent Tubes—Sorbent tubes are typically made of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH).

III. Cryogenic Condensates—Cryogenic condensation is a process that allows recovery of volatile compounds for reuse. The condensation process requires very low temperatures so that the volatile compounds can be condensed. Traditionally, chlorofluorocarbon (CFC) refrigerants have been used to induce condensation. Currently, liquid nitrogen is used in the cryogenic (less than $-160°$ C.) condensation process.

A dehumidifier that is within the scope of the present invention includes, but is not limited to, I. A device which draws moist air over cold refrigerated coils—using this approach, the air moisture condenses into droplets as it passes through cold refrigerated coils into a container. "Dried" air is then brought to its original temperature and returned to the sensing apparatus.

II. Silica Gel—is an amorphous form of silicon dioxide, which is synthetically produced in the form of hard irregular granules or beads. A microporous structure of interlocking cavities gives a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus, the higher the humidity of the surrounding air, the greater the amount of water that is adsorbed before equilibrium is reached. Silica gel is advantageous as a drying substance since the process of drying requires no chemical reaction and no by products or side effects.

III. Activated carbon—is formed by processing charcoal to an extremely porous carbon substance. Due to its high degree of microporosity the activated carbon possesses a very large surface area available for chemical reactions. Sufficient activation may be obtained solely from the high surface area, though further chemical treatments often enhance the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

According to one embodiment, the single-walled carbon nanotubes (SWCNTs) of the present invention are arranged in a random network configuration. In some embodiments, the network of SWCNTs can be fabricated by physical manipulation or in a self-assembly process. The term "self-assembly" as used herein refers to a process of the organization of molecules without intervening from an outside source. The self-assembly process occurs in a solution/solvent or directly on the solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Among these approaches, CVD coupled with photolithography has been found to be the most versatile in the preparation of various carbon nanotube devices. In a CVD method, a transition metal catalyst is deposited on a silicon wafer in the desired pattern, which may be fashioned using photolithography followed by etching. The silicon wafer having the catalyst deposits is then placed in a furnace in the presence of a vapor-phase mixture of, for example, xylene and ferrocene. Carbon nanotubes typically grow on the catalyst deposits in a direction normal to the substrate surface. Various carbon nanotube materials and devices are now available from commercial sources.

Other CVD methods include the preparation of carbon nanotubes on silica ($SiO_2$) and silicon surfaces without using a transition metal catalyst. Accordingly, areas of silica are patterned on a silicon wafer, by photolithography and etching. Carbon nanotubes are then grown on the silica surfaces in a CVD or a plasma-enhanced CVD (PECVD) process. These methods permit the production of carbon nanotube bundles in various shapes.

The term "single walled carbon nanotubes" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by having one of its dimensions (referred to as the length of the nanotube) elongated with respect to the other dimension (which is characterized by its diameter). It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm). More preferably, the single-walled carbon nanotubes have diameters ranging from about 0.7 nm to about 50 nm and lengths ranging from about ranging from about 250 nm to about 1 mm. Even more preferably, the single-walled carbon nanotubes have diameters ranging from about 0.8 nm to about 10 nm and lengths ranging from about 0.5 micrometer (μm) to about 100 μm. Most preferably, the single-walled carbon nanotubes of the present invention have diameters ranging from about 0.9 nm to about 5 nm and lengths ranging from about 1 μm to about 50 μm.

According to certain embodiments, the surface of the single walled carbon nanotube is functionalized with non-polymeric organic molecules comprising insulating functional monomers which are essentially non-polar. Preferably, these small organic molecules form thin films (20-10,000 nm) on the surface of the nanotubes. The functionalization of the nanotubes with non-polar small organic molecules, according to the principles of the present invention, can be performed through chemical bonding or alternatively through surface adsorption.

In currently preferred embodiments, the functionalization of the carbon nanotubes can be achieved by any of the methods disclosed herein:

I. Random deposition of non-polymeric solution on solid surfaces. The deposition is performed by drop casting, spin coating, spray coating, and other similar techniques.

II. Langmuir-Blodgett or Langmuir-Schaefer techniques. The substrate is vertically plunged through self-organized/well-ordered 2D film of non-polymeric material at the air-subphase interface, wherein the latter being subsequently transferred onto it. Multiple plunging of the substrate through the 2D film of the non-polymeric material at the air-subphase interface, results in the fabrication of a 3D-ordered multilayer/s of non-polymeric film.

III. Soft lithographic techniques, including micro-contact printing (mCP), replica molding, micro-molding in capillaries (MIMIC), and micro-transfer molding (mTM). These methods are based on variations of self-assembly and replica molding of organic molecules and polymeric materials, for fabricating non-polymeric films from nanometer-scale to a mesoscopic scale (Whitesides et al., *J. Mater. Chem.*, 1997, 7, 1069-1074).

IV. Various combinations of Langmuir-Blodgett or Langmuir-Schaefer methods with soft lithographic techniques are used to produce patterned Langmuir-Blodgett films of non-polymeric material and transfer them onto solid substrates.

V. Printing on solid-state or flexible substrates using inject printer that is designated for printed electronics. In this method, a solution containing the non-polymeric material is used as a filling material (or "ink") of the printing head. Few examples on the printing technology are found in Holland et al., *Ink Maker*, 2005, 8, 83; Rogers, et al., *Nanolitho. Pattern. Tech. Microelect.*, 2005, 373, 76-119.

Coating with small organic molecules in the context of the present invention refers to functionalization of the single-walled carbon nanotubes with organic molecules having molecular weight of less than about 2,000 grams per mole (i.e., a MW of less than about 2000), more preferably less than about 1,500 grams per mole (i.e., a MW of less than about 1,500), and most preferably less than about 1,000 grams per mole (i.e., a MW of less than about 1,000).

In various embodiments, the small organic molecules which are used to modify the surface of the nanotubes include, but are not limited to, unsubstituted and substituted alkyl, cycloalkyl, alkenyl, alkynyl, aryl, heterocyclyl, heteroaryl, alkylaryl, alkylalkenyl, alkylalkynyl, alkylcycloalkyl, alkylheterocyclyl and alkylheteroaryl groups; combinations and derivatives thereof. The groups can be substituted by one or more of a carboxyl, an acyl, an amido, an ester, a cyano, a nitro, an azido, a halogen, a hydroxy, or a haloalkyl moiety.

An "alkyl" group refers to a saturated aliphatic hydrocarbon, including straight-chain, branched-chain and cyclic alkyl groups. In one embodiment, the alkyl group has 1-40 carbons designated here as $C_1$-$C_{40}$-alkyl. In another embodiment, the alkyl group has 1-30 carbons designated here as $C_1$-$C_{30}$-alkyl. In another embodiment, the alkyl group has 1-10 carbons designated here as $C_1$-$C_{10}$-alkyl. Exemplary alkyl groups include ethyl, propyl, butyl, pentyl, heptyl, octyl, decyl, dodecyl, undecyl, tridecyl, tetradecyl, pentadecyl, hexadecyl, heptadecyl, octadecyl, nonadecyl, tricosyl, docosyl, tetracosyl, pentacosyl, hexacosyl, octacosyl and nonacosyl. A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like.

An "alkenyl" group refers to an aliphatic hydrocarbon group containing a carbon-carbon double bond including straight-chain, branched-chain and cyclic alkenyl groups. In one embodiment, the alkenyl group has 2-40 carbon atoms. In another embodiment, the alkenyl group has 2-30 carbon atoms in the chain. In another embodiment, the alkenyl group has 2-10 carbon atoms in the chain. Exemplary alkenyl groups include ethenyl, propenyl, n-butenyl, i-butenyl, 3-methylbut-2-enyl, n-pentenyl, heptenyl, octenyl, cyclohexylbutenyl, decenyl, dodecynyl, undecenyl, tridecenyl, tetradecenyl, pentadecenyl, hexadecenyl, heptadecenyl, octadecenyl, nonadecenyl, tricosenyl, docosenyl, tetracosenyl, pentacosenyl, hexacosenyl, octacosenyl and nonacosenyl.

An "alkynyl" group refers to an aliphatic hydrocarbon group containing a carbon-carbon triple bond including straight-chain and branched-chain. In one embodiment, the alkynyl group has 2-40 carbon atoms in the chain. In another embodiment, the alkynyl group has 2-30 carbon atoms in the chain. In another embodiment, the alkynyl group has 2-10 carbon atoms in the chain. Exemplary alkynyl groups include ethynyl, propynyl, n-butynyl, 2-butynyl, 3-methylbutynyl, n-pentynyl, heptynyl, octynyl, decynyl, dodecynyl, undecynyl, tridecynyl, tetradecynyl, pentadecynyl, hexadecynyl, heptadecynyl, octadecynyl, nonadecynyl, tricosynyl, docosynyl, tetracosynyl, pentacosynyl, hexacosynyl, octacosynyl and nonacosynyl.

An "aryl" group refers to an aromatic monocyclic or multicyclic ring system. In one embodiment, the aryl group has 6-10 carbon atoms. The aryl is optionally substituted at least one "ring system substituents" and combinations thereof, and are as defined herein. Exemplary aryl groups include phenyl, naphthyl, anthracene, azulene, decacyclene, chrysene, corannulene, phenanthrene, triphenylene, benzo[a]pyrene, coronene, naphthacene, pentacene, pyrene, and ovalene.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, iso-quinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like.

A "heterocyclic ring" or "heterocyclyl" group refers to five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Preferred heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein.

"Ring system substituents" refer to substituents attached to aromatic or non-aromatic ring systems including, but not limited to, halo, ($C_1$-$C_{40}$)alkyl, ($C_2$-$C_{40}$)alkenyl, ($C_2$-$C_{40}$)alkynyl, ($C_6$-$C_{10}$)aryl, ($C_5$-$C_{10}$)heteroaryl, —CN, —$CF_3$, —$NO_2$, —OH, ($C_1$-$C_8$)alkoxy, —O($CH_2$)$_n$NRR', —OC(O)R, —OC(O)NRR', —O($CH_2$)$_n$OR, —$CH_2$OR, —NRR', —C(O)NRR', —C(O)OR and —C(O)R, wherein R and R' are H, alkyl, cycloalkyl, aralkyl, alkaryl, aryl and the like.

Each of the groups defined hereinabove can be unsubstituted or substituted through available atoms with one or more groups selected from carboxyl, acyl, amido, ester, cyano, nitro, azido, halogen, hydroxy, and haloalkyl.

The term "carboxy" or "carboxyl" moiety refers carboxylic acid and derivatives thereof including in particular, ester derivatives and amide derivatives.

The term "acyl" as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

The term "halogen" or "halo" as used herein alone or as part of another group refers to chlorine, bromine, fluorine, and iodine.

The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chi orodifluoromethyl, pentafluoroethyl, 1,1-difluoroethyl bromomethyl, chloromethyl, fluoromethyl, iodomethyl, and the like.

The term "amide" or "amido" moiety refers to a —C(O) NRR' group wherein R and R' are independently selected from hydrogen, alkyl and aryl.

The small organic molecules as well as the substituted small organic molecules, according to the principles of the present invention, are essentially non-polar. The term "non-polar" or "essentially non-polar" as used herein refers to molecules having a dipole moment of less than about 1 Debye, more preferably less than about 0.75 Debye, and most preferably less than about 0.5 Debye. According to the principles of the present invention, the dipole moment values refer to the polarity of the small organic molecules when attached to the single-walled carbon nanotubes.

In currently preferred embodiments, the small organic molecules used to modify the surface of the nanotubes include, but are not limited to, propyl gallate, anthracene, tetracosanoic acid, tricosane, 3-methyl-2-phenyl valeric acid, tris(hydroxymethyl)nitro-methane, tetracosane, dioctyl phthalate, tetracosanoic acid, 1.2.5.6.9.10-hexabromo-cyclododecane, pentadecane, combinations and derivatives thereof.

In another currently preferred embodiment, the small organic molecules used to modify the surface of the nanotubes include, but are not limited to, hexa-peri-hexabenzo-coronene (HBC) molecules which are unsubstituted or substituted by any one of 2-ethyl-hexyl(HBC—$C_{6,2}$), 2-hexyl decane(HBC—$C_{10,6}$), 2-decyl tetradecane(HBC—$C_{14,10}$), and dodecane(HBC—$C_{12}$).

In yet other embodiments, the small organic molecules used to modify the surface of the nanotubes include, but are not limited to, four main groups of organic compounds and combinations thereof. The first includes alkanes with linear or branched chains having different chain lengths ($C_1$-$C_{40}$), such as, but not limited to, trioctane, tetradecane, pentadecane, heptadecane, octadecane, and the like. The second group includes various sub-groups of alkanes, each having a substantially similar length but different branching. Non-limiting examples of the second group include dodecane, undecane, tridecane, tetradecane, pentadecane, hexadecane, heptadecane, octadecane, nonadecane, tricosane, docosane, tetracosane, pentacosane, hexacosane, octacosane and nonacosane derivatives such as, but not limited to, (a) 2,2-dimethyldodecane, 3-ethyl-3-methyl-undecane, 3-methyltridecane, and n-tetradecane; (b) 5-ethyl-5-methyltri-decane, 2,2-dimethyltetradecane, 3-ethyl-3-methyltridecane, and 3-methylpentadecane; (c) 5-ethyl-5-methyl-pentadecane, 2,2-dimethylhexadecane, and 3-methylheptadecane; (d) 3-ethylheptadecane, 5,5,7,7-tetraethylun-decane, and 5-butyl-5-ethyl-tridecane; (e) 5,5-diethylheptadecane, 5-ethyl-nonadecane, and 3,3-dimethylnonadecane; (f) 5,5,11,11-tetraethylpentadecane, 5-butyl-5-ethylheptadecane, and 7,7-diethylnonadecane; (g) 6,6-diethyldocosane, 5-ethyl-5-methyltricosane, 2,2-dimethyltetracosane, and 3-ethyl-3-methyl-tricosane; (h) 3,3,17,17-tetraethylnonadecane, 5,5-diethyltricosane, 3,3-dimethylpenta-cosane, and 3,3-diethyltricosane; (i) 6,6-diethyltetracosane, 2,2-dimethylhexacosane, 5-butyl-5-ethyl-tricosane, 3-ethyl-3-methyl-pentacosane; (j) 3,3,19,19-tetraethylhenicosane, 5,5-diethylpentacosane, and 3,3-diethylpentacosane; and (k) 6,6-diethylhexacosane, 5,5-diethylheptacosane, 6,6-diethyloctacosane, and 5,5-diethylnonacosane. The third group includes aromatic compounds having different chain lengths and functionalities such as, but not limited to, bicycle [4.3.0]nona-3,6(1)-diene, azulene, anthracene, 2,3 benzanthracene, 2,3 benzofluorene, benz[e]-acephenanthrylene, benzo[a]pyrene, and benzo[e]pyrene. The forth group includes branched aromatic compounds, such as, but not limited to, 1,2 benzanthracene, benzo[ghi]perylene, 10-bis(phenylethynyl)anthracene, N,N'-bis(2,5-di-tert-butylphenyl)-3, 4,9,10-perylenedi-carboxymide, decacyclene, chrysene, corannulene, phenanthrene, triphenylene, benzo[a]pyrene, coronene, naphthacene, pentacene, pyrene, ovalene, and the like. Each possibility represents a separate embodiment of the invention.

According to additional embodiments, the array of sensors comprises a plurality of sensors between 2 to 1000 sensors, more preferably between 2 to 500 sensors, even more preferably between 2 to 250 sensors, and most preferably between 2 to 125 sensors in an array.

The sensors of the present invention can be configured as any one of the various types of electronic devices, including, but not limited to, capacitive sensors, resistive sensors, impedance sensors, field effect transistor sensors, and the like, or combinations thereof. Sensors based on carbon nanotubes provide unique electrical characteristics. Moreover, carbon nanotubes are particularly sensitive to environmental changes thus modulating the surface energies. These characteristics render them advantageous for detecting breath analytes.

According to yet other embodiments, the present invention provides apparatuses fabricated from random networks of SWCNTs. The random networks can be prepared using various techniques including, but not limited to, chemical vapor deposition (CVD) and traditional lithography, solvent suspension deposition, vacuum deposition, and the like. Within the scope of the present invention are arrays of devices fabricated on a single chip for multiplex and multiparametric applications.

In certain embodiments, the random network of carbon nanotubes is at least partially in contact with one or more conducting elements. The conducting elements may include a source and a drain electrode separated from one another by a source-drain gap. In other embodiments, the network of carbon nanotubes comprises nanotubes having a characteristic length substantially less than the source-drain gap, so that the nanotubes comprising the network substantially contact at most, only one of the source and drain electrodes. In yet other embodiments, the characteristic length is substantially greater than the source-drain gap, so that a substantial portion of the nanotubes comprising the network, contact both the source and the drain electrodes.

The system disclosed herein may further comprise a gate electrode wherein the sensor signal may be indicative of a certain property of the nanostructure under the influence of a gate voltage. Alternatively, the sensor signal may be indicative of a capacitance property of the nanostructure.

The sensor signal may be induced, according to the principles of the present invention by a change in any one or more of conductivity, resistance, impedance, capacitance, inductance, or optical properties of the sensors upon exposure to volatile organic compounds. Changes in the optical properties of the sensor network can be measured using e.g., spectroscopic ellipsometry. This technique measures the change in polarization upon reflection of polarized light from a surface. Without being bound by any theory or mechanism of action, the adsorption of analyte molecules induces changes in thickness of the random network SWCNTs. The change in thickness or roughness induces changes in polarization which can be recorded by the spectroscopic ellipsometry technique. The signal obtained is subsequently conveyed to a learning and pattern recognition analyzer to generate a result. In this manner no electrical contacts are required.

According to another embodiment, the present invention further provides a processing unit comprising a learning and pattern recognition analyzer, wherein the learning and pattern recognition analyzer receives sensor output signals and analyses them by various pattern analysis algorithms to produce an output signature. By comparing an unknown signature with a database of stored or known signatures, volatile organic compounds can be identified. The analyzer utilizes learning and pattern recognition algorithms comprising artificial neural networks, such as multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention. In a currently preferred embodiment, the algorithm used for processing the data is principal component analysis (PCA).

Additional algorithms suitable for identifying patterns of VOCs and quantifying their concentration include, but are not limited to, Fisher linear discriminant analysis (FLDA), soft independent modeling of class analogy (SIMCA), K-nearest neighbors (KNN), neural networks, genetic algorithms, and fuzzy logic algorithms. In some embodiments, the Fisher linear discriminant analysis (FLDA) and canonical discriminant analysis (CDA) and combinations thereof are used to compare the output signature and the available data from the database. After analysis is completed, the resulting information can be displayed on a display or transmitted to a host computer.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes.

In operation, when a neural network is combined with a sensor array, the sensor data is propagated through the networks. In this manner, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

In particular embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Specifically, PCA compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a proportional constant. Another relationship between matrices is that they share principal components in common, but their eigenvalues differ. The mathematical technique used in PCA is called eigen analysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

According to another aspect, a method for determining the composition and concentration of volatile organic compounds in a sample, comprising exposure of the sensors of the apparatus to the sample and using pattern recognition algorithms in order to identify and possibly quantify desired VOCs in a given sample, is provided in the present invention.

In yet another aspect, the present invention provides a method for diagnosing a disease in a subject, comprising: (a)

providing a system comprising an apparatus comprising an array of chemically sensitive sensors of single walled carbon nanotubes coated with small organic molecules, and a processing unit comprising a learning and pattern recognition analyzer wherein the learning and pattern recognition analyzer receives sensor output signals from the apparatus and compares them to stored data, (b) exposing the sensor array of the apparatus to the breath sample of the subject, and (c) using pattern recognition algorithms to detect volatile organic compounds in the sample indicative of a disease in the subject.

The system of the present invention provides the detection of a single analyte breath biomarker as well as the detection of a plurality of breath biomarkers and the unique pattern of VOCs which characterizes a particular disease or disorder. In additional embodiments, the pattern of VOC comprises analytes selected from the group consisting of trimethylbenzene, styrene, decane, octane, and 1-hexene. Each possibility represents a separate embodiment of the invention.

Encompassed within the scope of the present invention are functionalized SWCNT sensors in which the functional group is tailor-made to allow for specific identification of compounds selected from vapors of volatile organic compounds. The technology of the present invention provides fine tuning of the apparatuses through modifying the functional groups attached to the SWCNTs to high density functionalities which allow better signal/noise ratios. Tailoring of the functional groups provide sensitive as well as selective analyte responses. Such refined tailoring can be obtained by using non-polymer-based sorption phases in order to provide discrimination between subtle differences in molecular structures and unique patterns of the analytes to be detected.

GC-MS studies have shown that volatile $C_4$-$C_{20}$ alkanes and certain monomethylated alkanes and benzene derivatives appear to be elevated in instances of cancer. The compounds of interest are generally found at 1-20 ppb in healthy human breath, but can be seen in distinctive mixture compositions at elevated levels from 10-100 ppb in the breath of cancer patients. The VOC levels are elevated even at the early stages of the disease, since they reflect a change in the human body chemistry, rather than being solely dependent on the size of the cancerous tumor. Also, biomarkers of a specific disease (e.g., lung cancer) have distinctive mixture compositions/patterns that are different from mixture compositions/patterns of other diseases (e.g., breast cancer).

It is explicitly intended that the present invention encompass the detection of breath biomarkers from a wide variety of medical conditions. The medical conditions that can be diagnosed according to the principles of the present invention comprise indications which are induced due to oxidative stress. The oxidative stress can be caused by the exposure to oxidizing agents, increased oxygen exposure, oxygen-induced degeneration or disease, reperfusion injury, ionizing radiation, carcinogenic agents, chemotherapeutic agents, mutagenic agents and laser irradiation. In particular, the biomarker patterns which can be detected, according to the principles of the present invention are characteristic of various diseases and disorders including cancer, arthritis (arthritic conditions), atherosclerosis, kidney diseases, type 2 diabetes, chronic obstructive pulmonary disease (COPD), age related macula degeneration (AMD), neurodegenerative diseases including Alzheimer's disease, Parkinson's disease and amyotrophic lateral sclerosis (ALS). Each possibility represents a separate embodiment of the invention.

Currently preferred is the diagnosis of cancer using the system of the present invention. Exemplary cancers include, but are not limited to, lung cancer, prostate cancer, breast cancer, skin cancer, colon cancer, pancreatic cancer, lymphoma, leukemia, head and neck cancer, kidney cancer, ovarian cancer, bone cancer, liver cancer and thyroid cancer. In one particular embodiment, the present invention provides a method of diagnosing lung cancer in a subject.

Additionally, other medical conditions can also be diagnosed using the system of the present invention including, but not limited to, metabolic disorders, hypercholesterolemia, gastrointestinal infections, digestive processes, liver and kidney dysfunction, cardiac disorders, cardiovascular disease, gum disease, halitosis, blood component levels, oral infections, periodontal diseases, ketosis, yeast infections, pneumonia, lung infections, sexually transmitted diseases, vaginitis, nephritis, bilirubin production, and phenylketonuria.

According to the principles of the present invention, the biomarkers to be detected are non-polar biomarkers indicative of various disorders as defined hereinabove. It is to be understood that disorders which involve tissue inflammation and immune responses (e.g., asthma) which are characterized by polar biomarkers are explicitly excluded form the scope of the present invention.

The apparatuses of the present invention could be integrated in a watch or cellular phone, as a warning system for the initiation of a disease in the body of an individual. Due to the miniaturized dimensions (10-100 nanometers to a few micrometers) and low power consumption, the apparatuses are easily portable and further allow for wireless integration possibly within a single chip.

The system of the present invention can also be used in many different applications. These applications include, but are not limited to, environmental toxicology and remediation, materials quality control, product quality monitoring for food/beverage/agriculture, environmental monitoring for hazardous leak/spill detection and identification, cosmetic/perfume applications, chemical/plastics/pharmaceuticals applications, diesel/gasoline/aviation fuel identification etc.

The principles of the present invention are demonstrated by means of the following non-limitative examples.

EXAMPLES

Example 1

Fabrication of Sensors of Random Network of Single-Walled Carbon Nanotube Chemiresistors P-type semiconducting single-walled carbon nanotubes (SWCNTs) having >90% purity were obtained from ARRY international LTD (Germany). The nanotubes were characterized by scanning electron microscopy to possess an average diameter of 1.5 nm and length of 7 μm. SWCNTs were dispersed in DMF using sonication followed by ultracentrifugation. In order to obtain adherence of the SWCNTs on a surface, a degenerative p-doped silicon wafer coated with a 2,000 nm thick $SiO_2$ film was inverted and grazed against the interface of a SWCNTs solution. While still coated with solution, the substrate was blown with a stream of dry $N_2$. This resulted in an optically homogeneous thin film of DMF and SWCNTs. The substrate was then rinsed with deionized water and dried again. The process was repeated several times until the desired resistance (10KΩ-10MΩ) was achieved. The deposition of the SWCNT random network was then followed by the evaporation of 50 nm Pd electrodes through an interdigital shadow mask.

Example 2

Characterization of the Fabricated Sensors

The fabricated sensors were characterized under a scanning electron microscope. FIG. 1 shows the random SWCNTs network between two adjacent Pd electrodes. The SWCNTs clearly form a random network configuration which is characterized by the many paths by which the SWCNTs connect the two Pd electrodes together. Without being bound by any theory or mechanism of action, the connection of electrodes through many SWCNTs paths suggests that highly interconnected SWCNT arrays will be electrically continuous having electronic properties that depend on the level of interconnectivity and on the electronic properties of the constituent nanotubes.

Example 3

Functionalization of the Single-Walled Carbon Nanotubes

The single-walled carbon nanotubes were functionalized after the preparation of the fabricated apparatus. The following functionalizing organic molecules were used: dioctyl phthalate ($C_{24}H_{38}O_4$) plasticizer, propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_5O$, tetracosanoic acid ($C_{24}H_{48}O_2$), 1.2.5.6.9.10-hexabromo-cyclododecane ($C_{12}H_{18}Br_6$), and pentadecane ($C_{15}H_{32}$), all purchased from Sigma-Aldrich.

Functionalization was performed by drop casting of a single drop of $10^{-3}$M solution of the different functional monomers in THF on top of the apparatus. The apparatus was then dried for 2 hours in a fume hood at an ambient temperature. The apparatus was placed for 1-6 hours in an oven at 50° C.

Example 4

Electronic Response Measurements

The sensors were mounted into a custom PTFE circuit board with 10 separated sensors sites. The board was then mounted into a stainless steel test chamber having a volume of less than 100 cm³. An Agilent Multifunction switch 34980 controlled by USB was used to choose the active sensor at any given time. A Stanford Research System SR830 DSP Lock-in amplifier which was controlled by an IEEE 488 control bus was used to supply the AC voltage signal and measure the corresponding current. The device allowed for measuring normalized conductance response values as small as 0.1% for resistance calculations of the corresponding sensor. The entire system was controlled by a custom Labview program.

Figure 2:
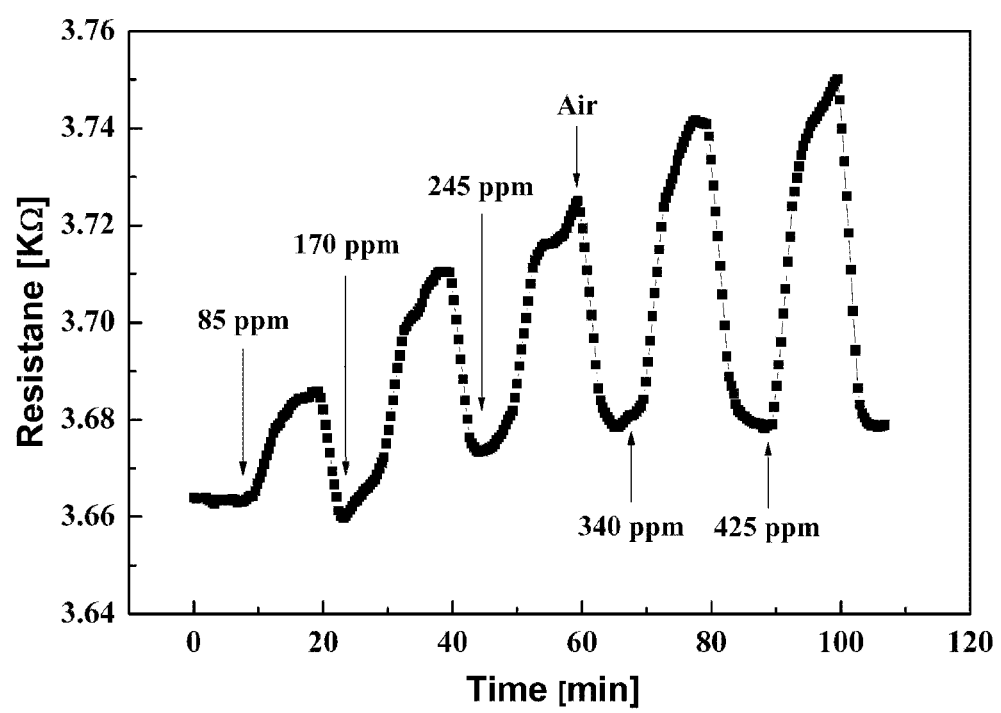
FIG. 2 is a graph of the response of a SWCNT sensor coated with propyl gallate to varying decane concentrations.

FIG. 2 shows the chemiresistance response of a SWCNT sensor coated with a monolayer of propyl gallate (hereby, S1) that was exposed to different decane concentrations. There is an essentially linear correlation between the response obtained and the concentration of decane. Furthermore, the response of the sensors was essentially immediate upon exposure to the vapor analyte, and fully reversible upon switching back to zero vapor analyte (purified, dry air). The response was obtained for a wide variety of concentrations with signal-to-noise ratio typically larger than 10:1.

Figure 3:
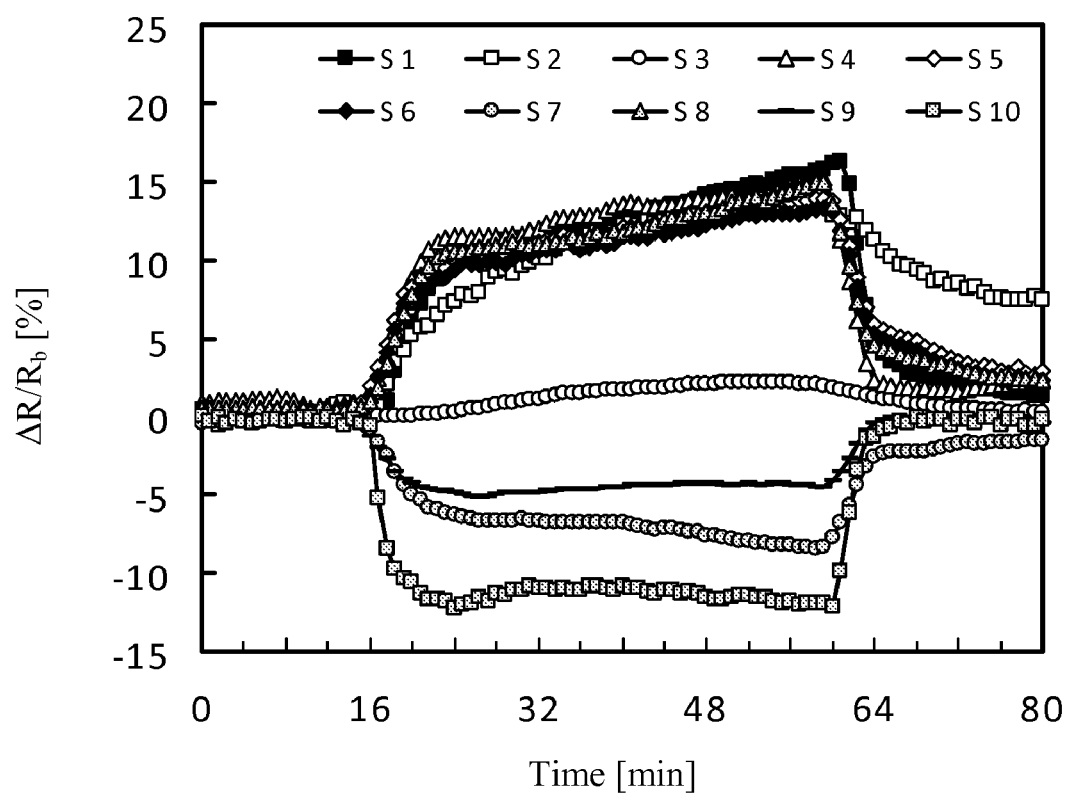
FIG. 3 is a graph of relative differential resistance responses, $\Delta R/Rb$, of a network of SWCNTs coated with different organic monomer films, to 0.5 Po trimethylbenzene vapors. Rb is the baseline resistance of the detector in the absence of an analyte; $\Delta R$ is the baseline-corrected steady-state resistance change upon exposure of the detector to an analyte.

FIG. 3 shows the relative differential resistance responses of a network of SWCNTs coated with films of small organic molecules as indicated in Table 1, to trimethylbenzene vapors at concentrations of 0.005 Po (the saturated vapor pressure of the analyte at room temperature). Not all coated SWCNTs responded in a similar manner. Instead, some functionalized SWCNTs produced opposite responses. Without being bound by any theory or mechanism of action, these differences might be attributed to various physical and chemical characteristics of the sensors. Possible mechanisms include charge transfer from adsorbed species, modifications of contact work functions, and carrier scattering by adsorbed species.

TABLE 1

Sensor symbols of SWCNTs coated with different organic monomers

| Sensor Symbol | Coatings |
| --- | --- |
| S1 | Propyl gallate ($C_{10}H_{12}O_5$) |
| S2 | Anthracene ($C_{14}H_{10}$) |
| S3 | Tetracosanoic acid ($C_{24}H_{48}O_2$) |
| S4 | Tricosane ($C_{23}H_{48}$) |
| S5 | 3-methyl-2-phenyl valeric acid ($C_{12}H_{16}O_2$) |
| S6 | Tris(hydroxymethyl)nitro-methane ($C_4H_9NO_5$) |
| S7 | Tetracosane ($C_{24}H_{50}$) + dioctyl phthalate(($C_{24}H_{38}O_4$) (3:1 w/w) |
| S8 | Tetracosanoic acid ($C_{24}H_{48}O_2$) + dioctyl phthalate(($C_{24}H_{38}O_4$) (3:1 w/w) |
| S9 | 1.2.5.6.9.10-hexabromo-cyclododecane ($C_{12}H_{18}Br_6$) + dioctyl phthalate($C_{24}H_{38}O_4$) (3:1 w/w) |
| S10 | Pentadecane ($C_{15}H_{32}$) + dioctyl phthalate ($C_{24}H_{38}O_4$) (3:1 w/w) |

Example 5

Identification of Biomarkers from Healthy Subjects and Lung Cancer Patients Alveolar breath was collected from individuals suffering from lung cancer and from healthy subjects by the off-line method recommended by the ATS/ERS (Silkoff et al., *Am. J. Respir. Crit. Care Med.*, 2005, 171, 912-930). Particularly, the subjects inhaled to total lung capacity through a mouthpiece that contained a cartridge on the aspiratory port, which removed more than 99.99% of airborne VOCs during inspiration, thus clearing the inhaled air of any ambient VOC contaminants. Immediately after, subjects exhaled against 10-15 cm $H_2O$ pressure to ensure closure of the vellum in order to exclude nasal entrainment of gas. The exhaled gas was collected through a separate exhalation port of the mouthpiece into a non-reactive Mylar gas-sampling bag (purchased from Eco Medics), which was previously cleaned with nitrogen gas. A minimum of five analyses were performed on the exhaled breath of each volunteer. Fifty people between the ages of 28-60 were included in this study, of which 25 were healthy subjects and 25 had stage-4 lung cancer. All volunteers were previously clinically diagnosed using various diagnostic methods including bronchoscope biopsy, computed tomography (CT) scan and pulmonary puncture. None of the lung cancer patients had received chemotherapy and/or other treatments before breath samples were collected.

The collected breath samples from individuals with lung cancer and from healthy subjects were analyzed with GC-MS combined with solid phase micro-extraction (SPME). The SPME technique was used for pre-concentrating the VOCs in the breath samples. A manual SPME holder with an extraction fiber coated with polydimethylsiloxane (PDMS; purchased from Sigma-Aldrich) was inserted into the Mylar bag. Between 500 and 1,000 cm³ of breath sample was concentrated via the SPME method and delivered to a GC-MS using a manual SPME holder. The extracted fiber in the manual SPME holder was inserted into a GC injector of the splitless model. The oven temperature profile was 60° C., 2 minutes, 8° C./minute to 100° C., 15° C./minute to 120° C., 8° C./minute to 180° C., 15° C./minute to 200° C., and 8° C./minute to 225° C. A capillary column H5-5MS 5% Phenyl Methyl Siloxane (30 m length, 0.25 mm i.d., 0.25 μm thickness) was used. The column pressure was set to 8.22 psi, and initial flow was 1.0 mL/minute. Eventually, the molecular composition of the VOCs was determined via the Standard Modular Set.

Figure 4A:
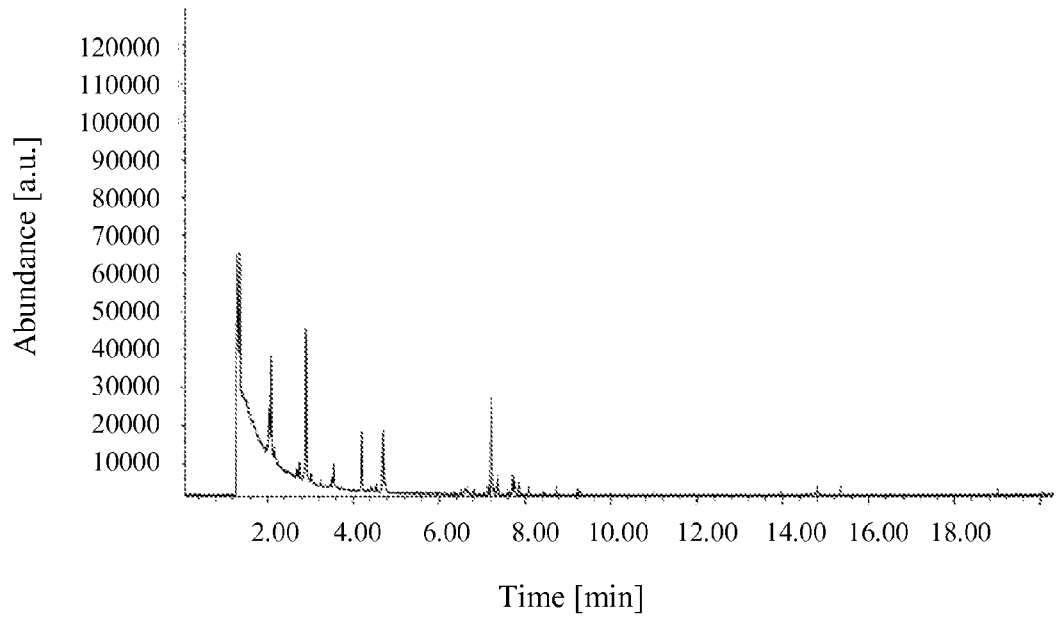
FIGS. 4A-4B are representative GC-MS spectra of exhaled breath of healthy individuals (4A) and of patients having lung cancer (4B).
Figure 4B:
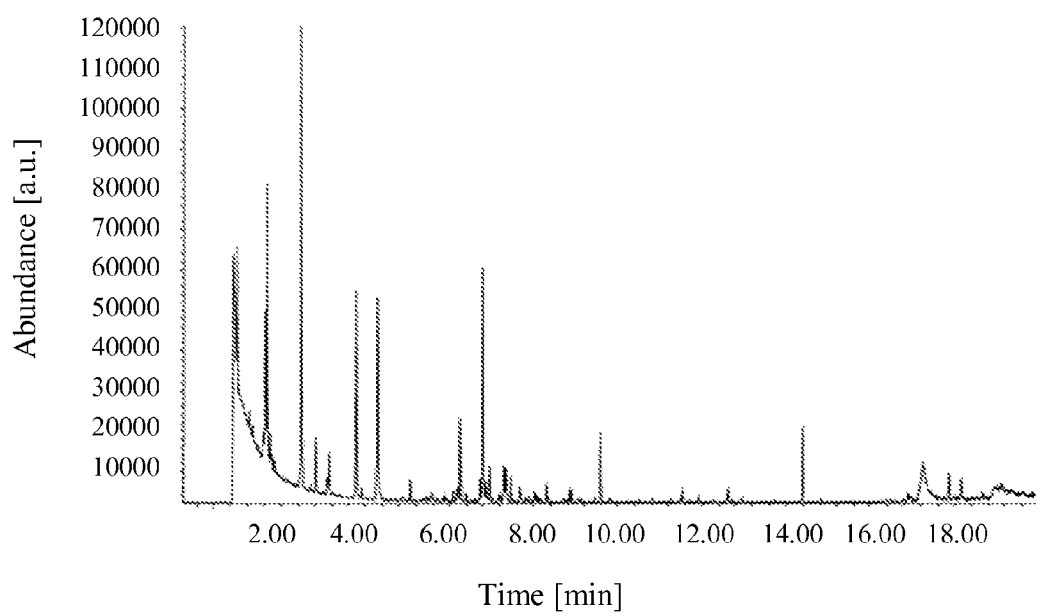

Representative GC-MS spectra of exhaled breath of healthy individuals and patients with lung cancer are presented in FIGS. 4A and 4B, respectively. The GC-MS analysis showed that several breath VOCs appear to be elevated in instances of lung cancer, mostly $C_4$-$C_{20}$ straight chain alkanes and mono-methylated alkanes, in addition to certain benzene derivatives. Part of these compounds are generally found in healthy human breath, but can be seen in distinctive mixture compositions and at elevated levels in the breath of cancer patients. The most significant VOCs that were representative of the majority of samples from lung cancer patients were found to be trimethylbenzene, styrene, decane, octane, and 1-hexene.

Example 6

Detection of Simulated Biomarkers by Coated Single-Walled Carbon Nanotube Detectors Simulated biomarkers were used instead of direct exposure to exhaled breath of lung cancer patients to precisely determine: (I) the signature of each individual cancer volatile biomarker on the developed array of sensors; (II) the correlation between the sensitivity and specificity of the sensors for each individual VOC biomarker to its signature in a pattern (or mixture) of other compounds; and (III) the necessary iterative feedback on sensors viability without the intervention of (disruptive) parameters such as patients' diet, metabolic state, genetics, etc.

An array of random network of single-walled carbon nanotubes were coated with a variety of thin (200-500 nm in thickness) organic films. Non-polymeric organic compounds having different chain length, chain branching, aromatic configuration, and functional groups (Table 1) were used as the non-polar organic films for the detection of biomarkers indicative of lung cancer. A wide variety of functional groups was used as well as increased density of the non-polymeric functional groups in order to increase the interactions between the vapor molecules and the sorption material thus allowing for an increased amount of vapor sorption, as compared to polymer-based sorption phases.

Figure 5:
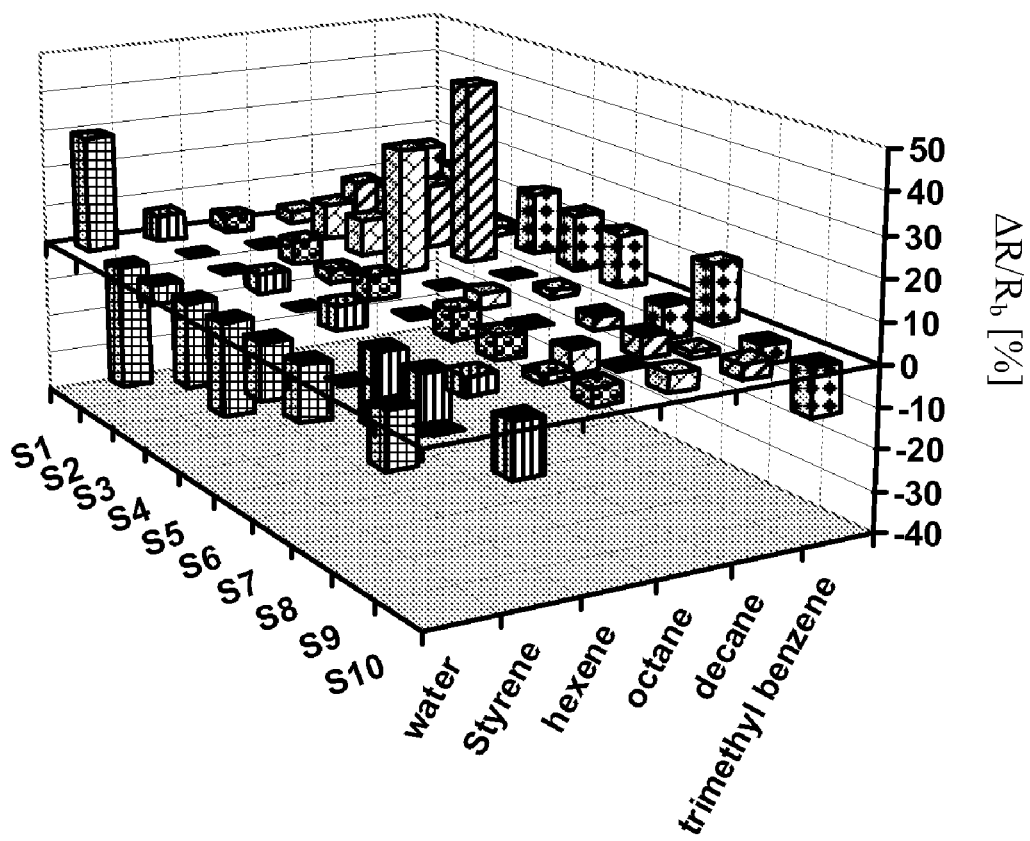
FIG. 5 is a diagram of response patterns for representative biomarkers.

The response ($\Delta R/Rb$, where Rb is the baseline resistance of the sensor in the absence of analyte, and $\Delta R$ is the baseline-corrected steady-state resistance change upon exposure of the sensor to an analyte) of a series of SWCNT sensors to the different lung cancer biomarkers at concentrations between 1 ppb and 100 ppm was first examined. In general, sorption of biomarkers showed change in resistance with exposure to an analyte. Part of the sensors showed increased resistance upon biomarker exposure whereas the other part showed decreased resistance upon exposure to certain biomarkers (FIG. 5).

Coating with small organic molecules produces increased sensitivity of the SWCNT detectors, in comparison to polymer-coated SWCNTs. Sensors coated with small organic molecules thus provide better discrimination between closely related alkane species and mixtures thereof. The use of an array of such highly sorptive films, therefore, readily provides distinct response fingerprints for compositionally different mixtures of VOCs, which is required for differentiating between the healthy breath samples and breath samples from lung cancer patients.

Example 7

Figure 6:
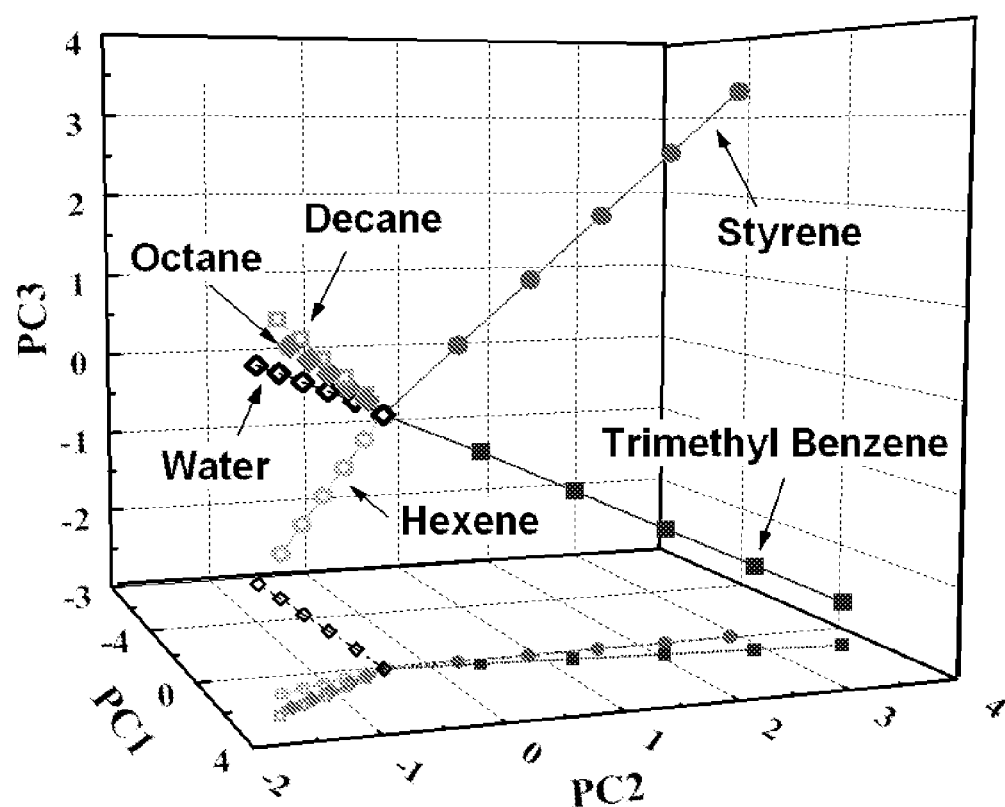
FIG. 6 represents the data obtained from an array of 10 detectors exposed to the representative VOC biomarkers of lung cancer in principal component space.

Detection of Simulated Biomarkers by Coated Single-Walled Carbon Nanotube Detector Arrays FIG. 6 presents the concentration-dependent $\Delta R/Rb$ response data for the entire detector array in principal component analysis (PCA) space. An array of 10 detectors was exposed to representative VOC biomarkers of lung cancer and to water at $P/P°=0.01$-$0.5$ in air. Exposure to water was performed in order to simulate the humidity effect in exhaled breath. The first three principal components depicted contained 92% of the total variance in the data. The linear lines contained >90% of the data for each analyte. Each VOC biomarker was presented 5 times to the array, with the order of presentation randomized over all repetitions of all test solvents. The projection of the principal component space on PC1 and PC2 is included for clarity.

Each test biomarker produced a unique signal response pattern, wherein the axes in principal component space are indicative of the biomarker and the pattern height is proportional to the biomarker concentration in the vapor phase. This behavior is further illustrated by normalizing the detector response patterns with respect to analyte concentration according to:

$$S_j=(\Delta R_j/R_{bj})(P°/P) \quad (1)$$

where Sj is the normalized signal for 10 sensor films exposed to 1,2,4-trimethyl benzene (>98% purity), styrene (>99.8% purity), decane (>95% purity), octane (>99.0% purity), and 1-hexene (>98% purity), each present at 0.001-0.5 P/P°. The characteristic Sj pattern of each test vapor was maintained, within experimental error, as the analyte concentration varied.

The sensor array response showed discrimination between the individual VOC biomarkers and water. Furthermore, the scores of hydrophobic molecules were all present on the positive side of the PC1 axis and scores of hydrophilic molecules were present on the negative side of the PC1 axis. The representative non-polar lung cancer biomarkers (e.g., 1-hexene, octane and decane) showed a negative PC2 score while the other biomarkers showed a positive PC2 score. Thus, a clear discrimination of lung cancer biomarkers was obtained using the apparatus and system of the present invention.

Example 8

Analysis of Complex Multi-Component (Bio) Chemical Media

Based on the GC-MS analysis of breath samples from healthy individuals and lung cancer patients (FIGS. 4A and 4B, respectively), simulated "healthy" and "cancerous" breath patterns at similar concentration levels were prepared in 80% Relative Humidity (RH), to simulate the background water vapor content in human breath. A mixture of 25.7 ppb styrene, 32.8 ppb 1,2,4-trimethyl benzene, 30 ppb decane, 22 ppb octane and 24 ppb 1-hexene with 80% RH, 21% $O_2$, 1 ppm CO, and 1% $CO_2$ was used to simulate "cancerous" breath (Chen et al., Sci. Technol., 2005, 16, 1535-1546). A mixture of 29 ppb decane with 80% RH, 21% $O_2$, 1 ppm CO, and 1% $CO_2$ was used to simulate "healthy" breath. Multiple exposures to each mixture were performed and data was obtained for the array of sensors. The conductance response of the 10 detectors after multiple exposures, averaging and principal component analysis (PCA) is shown in Table 2.

TABLE 2

ΔG/G$_b$ (%) responses of functionalized random network of SWCNT sensors to representative lung cancer biomarkers at P$_a$/P$_o$ = 0.004 concentration level.

| | TMB | Decane | Styrene | Hexene | Octane | Water |
|---|---|---|---|---|---|---|
| Propyl gallate (C$_{10}$H$_{12}$O$_5$) | −16.3 | −8.9 | −6.7 | −4.2 | −3.3 | 29.5 |
| Anthracene (C$_{14}$H$_{10}$) | −14.5 | −10.7 | — | — | −9.1 | 31.5 |
| Tetracosanoic acid (C$_{24}$H$_{48}$O$_2$) | −2.3 | −15.9 | — | −5.8 | −9.3 | 5.0 |
| Tricosane (C$_{23}$H$_{48}$) | −15.2 | −0.45 | −4.6 | −3.2 | −25.2 | 21.2 |
| 3-methyl-2-phenyl valeric acid (C$_{12}$H$_{16}$O$_2$) | −13.9 | — | — | −5.8 | — | 23.2 |
| Tris(hydroxymethyl)nitro-methane (C$_4$H$_9$NO$_5$) | −13.3 | −1.8 | −6.2 | — | −3.7 | 14.2 |
| Tetracosane (C$_{24}$H$_{50}$) + dioctyl phthalate((C$_{24}$H$_{38}$O$_4$) (3:1 w/w) | 8.3 | −3.4 | 18.5 | −7.0 | — | −13.9 |
| Tetracosanoic acid (C$_{24}$H$_{48}$O$_2$) + dioctyl phthalate((C$_{24}$H$_{38}$O$_4$) (3:1 w/w) | 14.7 | −5.3 | — | −6.1 | −6.2 | — |
| 1.2.5.6.9.10-hexabrormo-cyclododecane (C$_{12}$H$_{18}$Br$_6$) + dioctyl phthalate(C$_{24}$H$_{38}$O$_4$) (3:1 w/w) | 4.5 | −1.2 | 5.1 | −1.9 | — | −13.6 |
| Pentadecane (C$_{15}$H$_{32}$) + dioctyl phthalate (C$_{24}$H$_{38}$O$_4$) (3:1 w/w) | 7.9 | −2.01 | 13 | −4.2 | −4.4 | −35 |

Figure 7A:
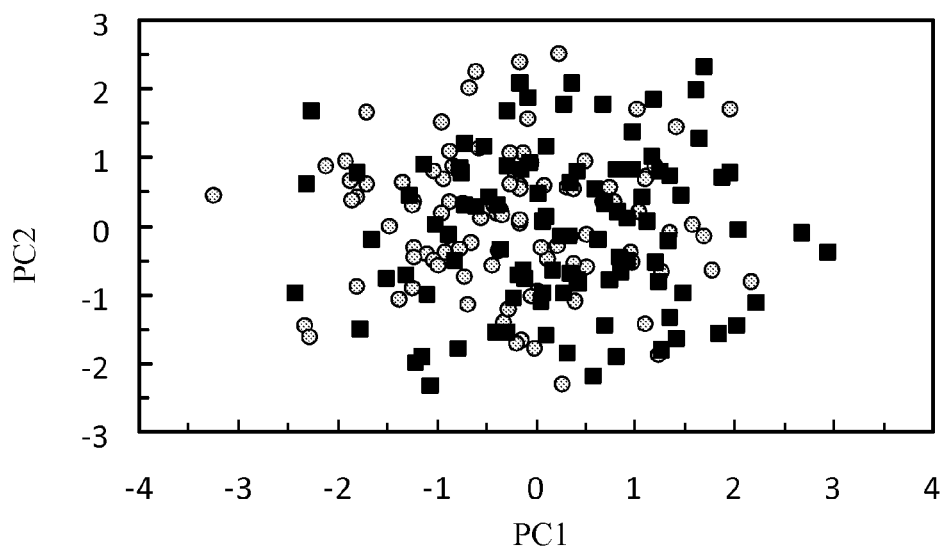
FIGS. 7A-7D represent the principal components score plots of an array of 10 sensors upon exposure to simulated "healthy" (circles) and "cancerous" (squares) patterns at (7A) 80% relative humidity (RH); (7B) 10% RH; (7C) 1% RH; and (7D) at 80% RH and pre-concentration (×50).
Figure 7B:
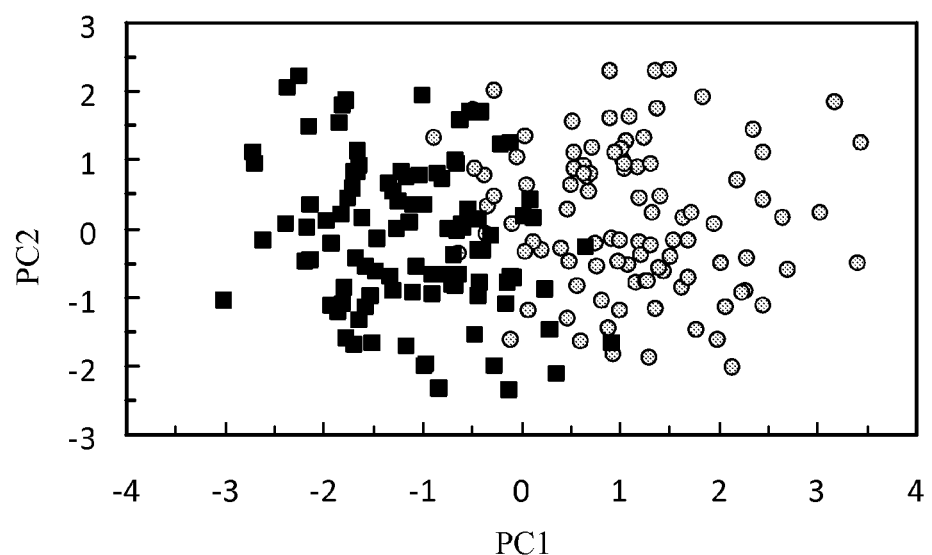
Figure 7C:
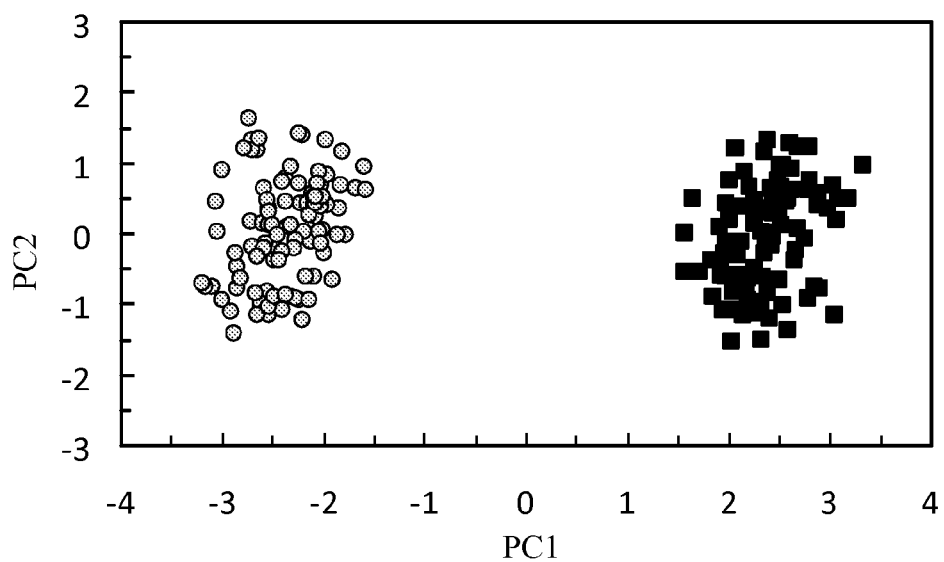
Figure 7D:
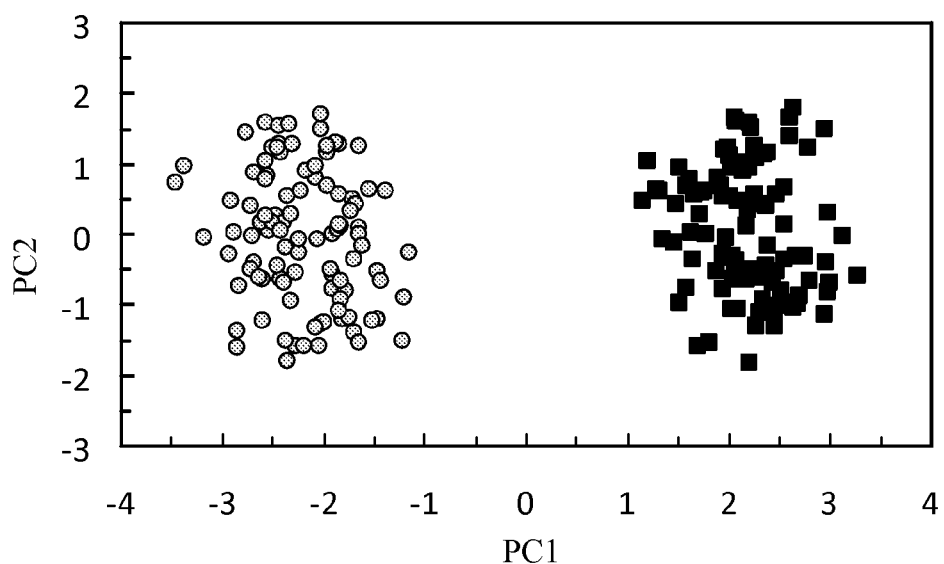

Principal component analysis of the obtained signal indicated that discrimination between simulated cancerous and healthy breath is rather difficult (FIG. 7A). Yet, gradual decrease of the relative humidity content from 80% to 10% formed two pattern recognition clusters, indicating a discrimination between the different breath samples (FIG. 7B). Further decreasing the RH from 10% to 1-5% formed well-separated clusters (FIG. 7C) indicating an excellent discrimination capability between simulated "healthy" and "cancerous" patterns. Alternatively, pre-concentrating the simulated breath at 80% RH by 50 times while leaving the water content constant (80% RH) resulted in an excellent discrimination between the "healthy" and "cancerous" patterns (FIG. 7D). Water molecules, which are found at high concentration levels in breath samples, have high chemical and electrical affinity towards SWCNTs. They thus interfere with VOC detection even when present at lower concentration levels. Bringing either the water molecules (by means of extraction) or the lung cancer VOC biomarkers (by means of pre-concentration) to comparable concentration levels allows good discrimination between the different breath states.

Finally, breath samples of healthy individuals and of lung cancer patients that were pre-concentrated by the SPME technique or extracted from water, were passed through a chamber containing the array of sensors of the present invention for sensor response. The PCA analysis of the resistance responses showed partially overlapping clusters, mostly due to different diets, metabolic and genetic states of the volunteers. Averaging the PCA data of the "healthy" and "cancerous" states, however, showed two well-separated clusters, similar those observed in FIGS. 7C and 7D, indicating differentiation between the two classes of breath samples.

Example 9

Sensing Apparatus

A computer-controlled automated flow system delivers pulses of simulated biomarker(s) vapor containing 1,2,4-trimethyl benzene, styrene, decane, octane, and 1-hexene. In addition to these representative VOCs indicative of lung cancer, water is used to simulate the saturated humidity in exhaled breath. The biomarkers are transferred to the detectors at controlled fractions and at regulated vapor pressure(s). Oil-free air is obtained from a house compressed air source (100±5 ppm of water vapor) regulated by a 5 L/minute mass flow controller. In a typical experiment, signals of sensor array elements are collected in a 10 minutes interval of clean laboratory air, followed by a 10 minutes interval of analyte vapors in air, and another 10 minutes interval of clean air to purge the system. Data analysis of the signals that are collected from all the sensors in the array is performed using standard principal component and cluster analysis.

Example 10

Fabrication of Sensors of Random Network of Single-Walled Carbon Nanotube Field Effect Transistors P-type semiconducting single-wall CNTs having an average diameter of 1.5 nm and length of 7 μm, with a purity of >90 wt %, were obtained from ARRY International Ltd. (Germany). The single-walled CNTs were dispersed in dimethylformamide (DMF), using sonication followed by ultracentrifugation. Then, a degeneratively doped p-type Si (100) substrate, 300 nm (in thickness) SiO$_2$ film was inverted and grazed against a surface of the single walled CNTs solution, so that a layer of solution remained on the surface. While still coated with solution, the substrate was blown with a stream of dry N$_2$. This resulted in an optically homogeneous thin film of DMF and CNTs. The substrate was then rinsed with deionized water and dried again. This process was repeated several times to yield the desired resistance.

On top of the electrically continuous, sub-monolayer thick random network of SWCNTs, ten pairs of 50 nm thick interdigitated Pd electrodes, with an effective channel length of 0.3 mm and a channel width of 4.5 mm, were deposited by electron-beam evaporation through a shadow mask in order to form field effect transistors of random network of SWCNTs for electrical testing. Following the patterning of the electrodes, 10 μl of 10 mM THF solution of tricosane (C$_{23}$H$_{48}$) or pentadecane (C$_{15}$H$_{32}$) with polar dioctyl phthalate (C$_{24}$H$_{38}$O$_4$) plasticizer (3:1 in mass) were casted on the contacted random network SWCNTs, dried for 2 hours in air at ambient temperature, and then heated to 50° C. in a vacuum oven. The SWCNTs of the present invention were functionalized with non-polar small organic molecules, according to the principles of the present invention, in order to study the charge transfer from/to the CNTs.

Example 11

Electronic Characterization of Random Network of Single-Walled Carbon Nanotube Field Effect Transistors The sensors of random network of single-walled carbon nanotube field effect transistors prepared according to Example 10 hereinabove, were electronically characterized.

The characterization was performed using a homemade setup which contained an automated, computer controlled flow system, capable of regulating the concentration of the analytes via their vapor pressure, and an exposure chamber which can accommodate up to 10 apparatuses. The concentration of the analytes was kept constant at $P_a/P_o=0.004$, where $P_a$ is the partial pressure of the analytes and $P_o$ is the saturated vapor pressure. An Agilent multifunction switch 34980 was used to subsequently address the apparatuses in the exposure chamber. A Stanford Research System SR830 DSP lock-in amplifier controlled by an IEEE 488 bus was used to supply the AC voltage signal and measure the corresponding current. This setup allows the measurements of normalized changes in conductance as small as 0.01%. Changes in the work function during exposure to the analytes were monitored under ambient conditions by measuring the electrical potential of contact-free surfaces relative to that of a gold reference, using a commercial Kelvin probe system (Ambient Kelvin Probe Package, KP Technology Ltd, UK). The Kelvin probe package includes a head unit with integral tip amplifier, a 2 mm tip, a PCI data acquisition system, a digital electronics module, a system software, an optical baseboard with sample and Kelvin probe mounts, a 1-inch manual translator, and a Faraday cage. The work function resolution of the system was 1-3 mV. Kelvin probe data was averaged from three or more different samples.

The electrical contacts obtained for this configuration provided an electrical conductance of ~0.1 $e^2/h$ (e: Electron charge, h: Planck's constant) at the intersection of two metallic SWCNTs, and Schottky barriers with a barrier height of ~$E_g/2$ at the intersection of a metallic SWCNTs and semiconducting SWCNTs. Highly interconnected CNT arrays were electrically continuous, with p-type electronic properties that depended on the level of interconnectivity and on the properties of the constituent SWCNTs. The resistance of the apparatuses was typically 200-400 KΩ at zero gate voltage, $V_G$.

Figure 8:
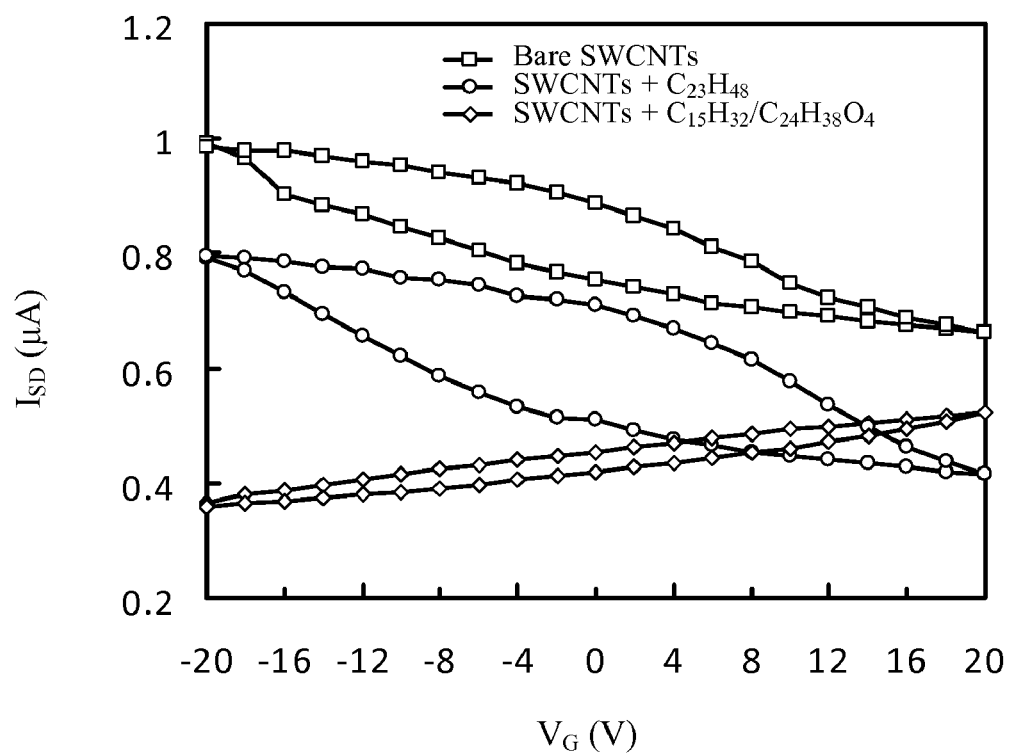
FIG. 8 is a graph of the gate-voltage $V_G$ dependence of $I_{SD}$ for bare (squares) and functionalized (circles and diamonds) random network SWCNT field effect transistors in air.

FIG. 8 displays the $I_{SD}$-$V_G$ (where $I_{SD}$ is the current measured between the source and drain) transfer characteristics of the apparatuses in air. The source-drain bias, $V_{SD}$, was kept constant at 0.2V. The bare random network of SWCNT field effect transistors (squares) showed p-type characteristics with low hysteresis. Functionalization with non-polar $C_{23}H_{48}$ monomers (circles) preserved the p-type transfer characteristics with no shift in the threshold voltage and larger hysteresis. The more polar $C_{15}H_{32}/C_{24}H_{38}O_4$ monomers (diamonds) showed n-type characteristics with practically no hysteresis. Without being bound by any theory or mechanism of action, the changes in hysteresis may be attributed to the sensitivity of the random network of functionalized SWCNTs to water vapors.

Example 12

Analyte Vapor Detection by Single-Walled Carbon Nanotubes Functionalized with Small Organic Molecules of Varying Polarities The apparatuses of functionalized random network of SWCNTs of Example 10 hereinabove, were exposed to decane (>98% purity; Sigma Aldrich Ltd.) as a non-polar (0 Debye) breath biomarker indicative of lung cancer and to 1,2,4-trimethyl benzene (TMB; >98% purity; Sigma Aldrich Ltd.) as a polar (1.16 Debye) lung-cancer biomarker. The apparatuses were used as a chemiresistors, namely, $V_{SD}$ was kept constant at 0.2 V and the gate was disconnected, while the baseline-corrected variation of the conductance, $\Delta G/G_b$, was measured as a function of time ($G_b$ is the baseline conductance of the apparatus in air and $\Delta G$ is the absolute change of the conductance upon exposure).

Figure 9:
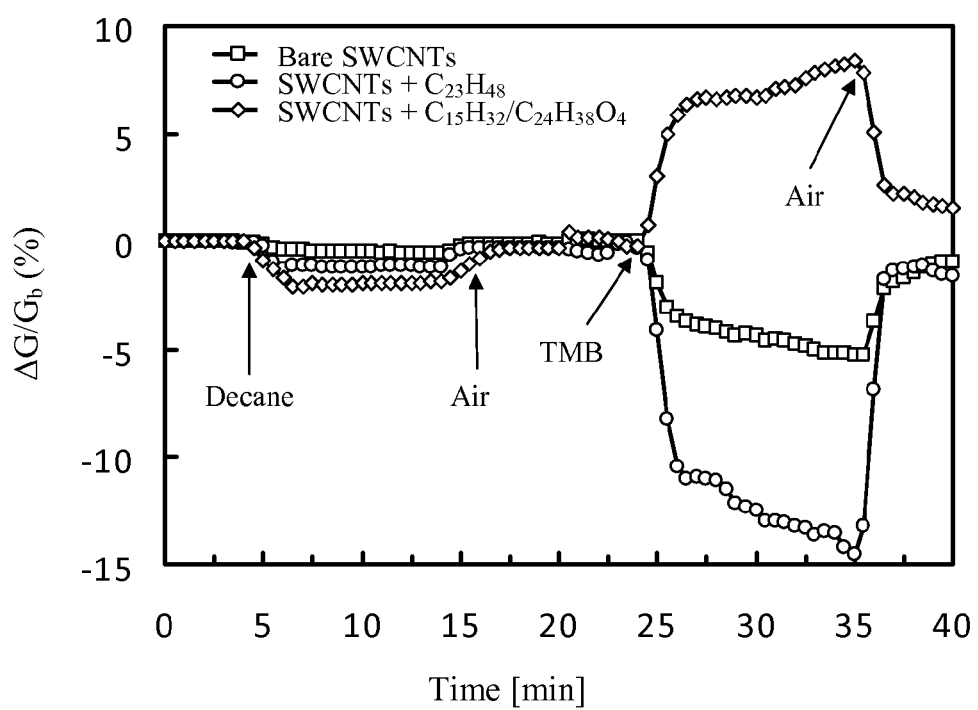
FIG. 9 is a graph of the conductance response, $\Delta G/G_B$, of bare (squares) and functionalized (circles and diamonds) random network SWCNT chemiresistors as a function of time at different chemical environments at $P_d/P_o=0.004$.

FIG. 9 displays the conductance response of three random networks of SWCNT apparatuses upon exposure to the representative polar and non-polar VOCs. All three apparatuses (bare, non-polar functionalized and polar-functionalized) responded rapidly with a small decrease in conductivity upon exposure to decane. When flushed with dry air after the exposure, the conductivity was rapidly and fully restored. It can be clearly seen that the functionalization enhances the response to decane. Specifically, the conductance decreased by 0.5% for bare CNTs (squares), 1% for $C_{23}H_{48}$-coated CNTs (circles), and 2% for $C_{15}H_{32}/C_{24}H_{38}O_4$-coated CNTs (diamonds).

Upon exposure to TMB, the response changed dramatically. Whereas the conductance of the bare CNT apparatus was reduced by 5% solely, a reduction of 15% for the $C_{23}H_{48}$-coated apparatus and an increase of 8% for the $C_{15}H_{32}/C_{24}H_{38}O_4$-coated apparatus were detected.

Figure 10:
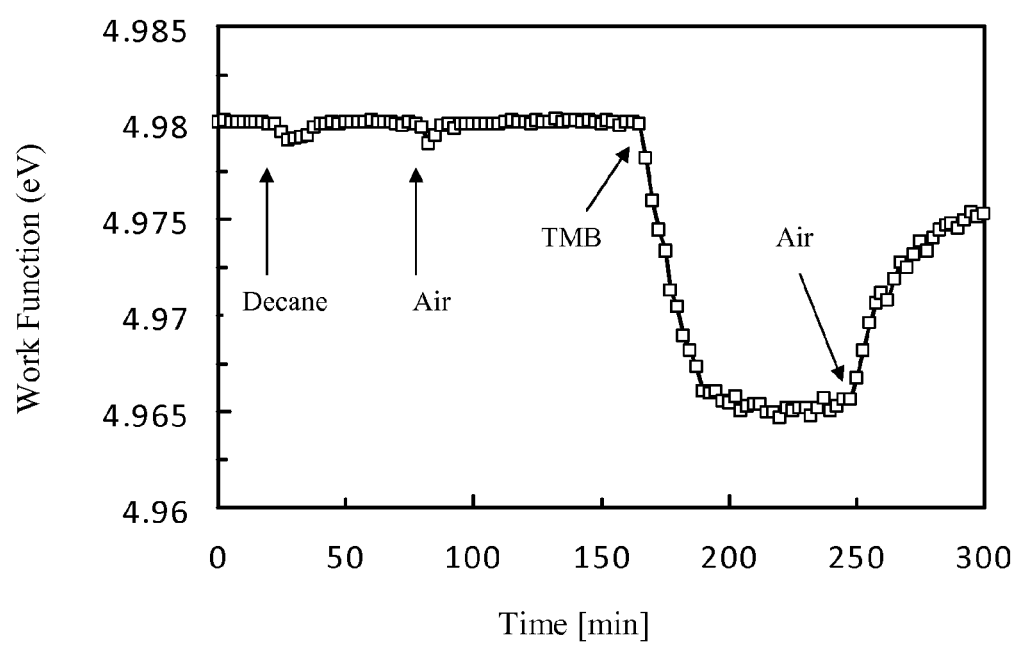
FIG. 10 is a graph of work function of bare random network of SWCNTs as a function of time at different chemical environments at $P_d/P_o=0.004$.

As control, the work function of bare random network of SWCNTs without electrodes upon successive exposure to decane and TMB vapors was determined (FIG. 10). A work function of 4.980±0.001 eV was measured in air. No measurable change in the work function when flushing the apparatus with decane was detected. In contrast, the work function decreased dramatically when bare SWCNT mesh was exposed to TMB, with no full recovery after purging with air. Without being bound by any theory or mechanism of action, this could be attributed to the lack of polarity of decane molecules wherein no charge transfer from the adsorbed decane molecules to the CNT mesh occurs and the work function remains unchanged, whereas TMB molecules act as an electron donors which interact strongly with the graphitic sidewalls of the CNTs through effective π-π-stacking, and thus decrease the work function. The conductance is therefore strongly influenced by charge transfer and carrier scattering wherein the conductance in p-type CNT apparatuses decreases, and the conductance in n-type CNT apparatuses increases when exposed to electron-donating analytes whereas the conductance in p-type CNT apparatuses increases and the conductance in n-type CNT apparatuses decreases when exposed to electron accepting analytes. When exposed to non-polar analytes wherein no charge transfer occurs, the conductance decreases both for p-type and n-type CNT apparatuses.

Hence, the functionalization of random network of SWCNTs with non-polar small organic molecules allows the detection of both non-polar as well as polar VOCs by providing measurable electronic response upon vapor adsorption whereas bare SWCNTs do not provide measurable electronic responses upon adsorption of non-polar VOCs. In particular, non-polar VOCs indicative of cancer, which are generally difficult to trace, can therefore be detected in random network of SWCNTs coated with tailored organic films.

Example 13

Analyte Vapor Detection by Single-Walled Carbon Nanotubes Functionalized with Small Organic Molecules Using Spectroscopic Ellipsometry The sensors of random network of single-walled carbon nanotube field effect transistors prepared according to Example 10 hereinabove, were optically characterized upon exposure to different analyte vapors. The changes in average thickness of bare and functionalized random network of SWCNT layers during exposure to the analytes were measured using spectroscopic ellipsometry.

Spectra were recorded over a range of 250-1700 nm at an incidence angle of 75°, using a spectroscopic phase modulated ellipsometry (M-2000U Automated Angle, J. A. Woollam Co., Inc., USA). The exact thickness of the $SiO_2$ layers was determined experimentally for every substrate prior to the deposition and functionalization of the random network-SWCNT layers. A three-phase-overlayer/$SiO_2$/Si model was used to extract an average thickness of the thin monomer/CNT composite layers. Areas of about 1×5 $mm^2$ with, local variations of the thickness were measured by spectroscopic ellipsometry. An increase in the average thickness upon exposure to the analyte vapors, measured at the same spot, was used to determine the amount of analytes adsorbed to the CNT mesh. A Cauchy dispersion of the refractive index for the monomer/CNT composite layers was assumed.

Only a small increase in thickness of bare SWCNT mesh after exposure to decane (30%) and to TMB (15%) occurred. In contrast, the thickness of the $C_{23}H_{48}$-coated mesh doubled, and the thickness of the $C_{15}H_{32}/C_{24}H_{38}O_4$-coated increased by a factor of 2.5 upon exposure to decane; and the thickness of the $C_{23}H_{48}$-coated increased by 30%, and the thickness of the $C_{15}H_{32}/C_{24}H_{38}O_4$-coated increased by 80% upon exposure to TMB.

The sensitivity and chemical selectivity to various VOCs indicative of cancer can be controlled by the swelling of the thin organic film coating the random network of SWCNTs. Hence, coating of the SWCNTs with different functional groups provides improved sensitivity for polar as well as non-polar VOCs indicative of cancer.

Example 14

Figure 11A:
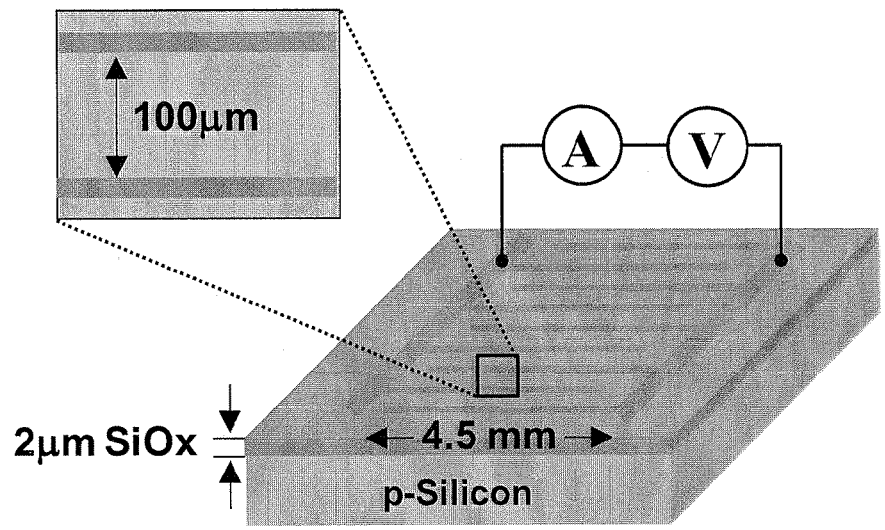
FIG. 11A is a schematic representation of the interdigitated electrodes used to fabricate the two terminal chemiresistors.
Figure 11B:
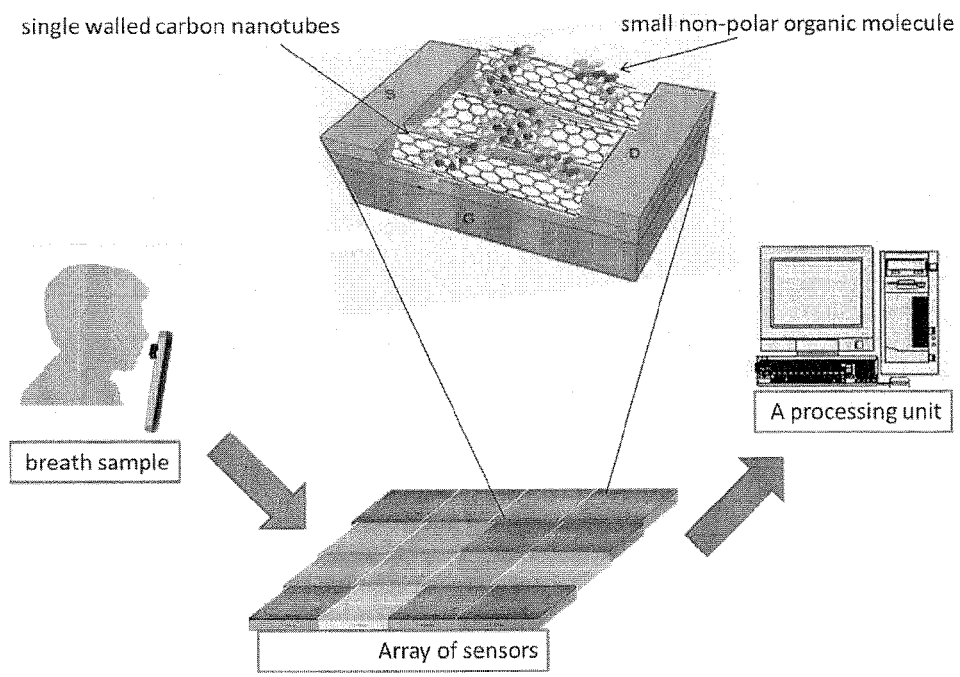
FIG. 11B is a schematic representation of the system of the present invention.

Fabrication of Apparatuses of Single-Walled Carbon Nanotubes Functionalized with Sponge-Like Structures of Hexa-Peri-Hexabenzocoronenes Derivatives The sensors were prepared on device quality, degeneratively doped p-type Si(100) wafers capped with a 2 μm thick thermally grown $SiO_2$ insulating layer. Ten pairs of 4.5 mm wide, interdigitated (ID) electrodes with an inter-electrode spacing of 100 μm were formed on the substrates by electron-beam evaporation of 5 nm Ti/Pd (5 nm/40 nm) through a shadow mask, as schematically illustrated in FIG. 11A. The sensors were fabricated according to Example 1 hereinabove. A non-limiting example in which the system of the present invention can be configured is illustrated in FIG. 11B. The apparatuses were slowly dried under ambient conditions for 10 minutes to enhance the self-assembly of the random network of SWCNTs. Then the apparatuses were heated to 150° C. for half an hour on a hot plate to evaporate the solvent. This process was repeated, when necessary, until a resistance of about 30 kΩ was achieved. The SWCNTs used were a mixture of about 30% metallic and about 70% semiconducting CNTs. The resistance of the apparatuses used was typically 30-40 KΩ at ambient air.

Figure 12A:
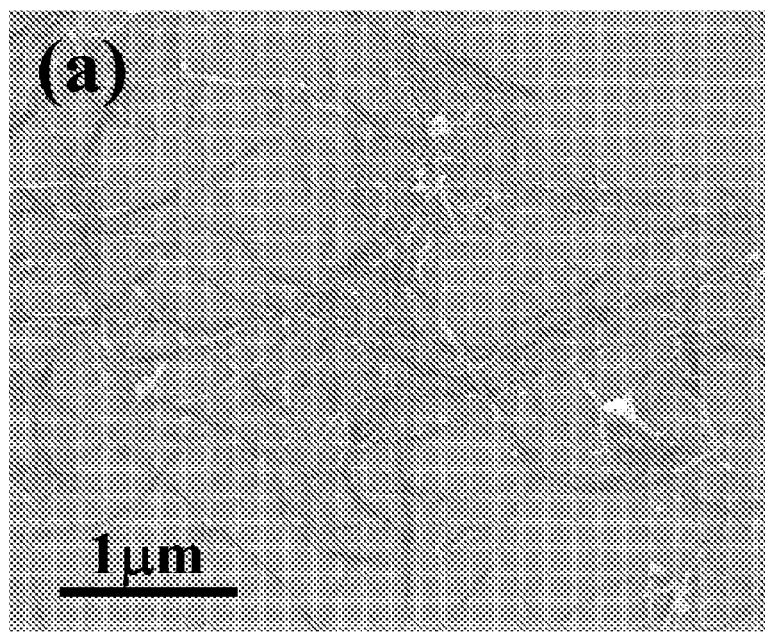
FIGS. 12A-12C are scanning electron micrographs of (12A) random network SWCNT cast from DMF solution; (12B) HBC—$C_{6,2}$ structures casted from $10^{-3}$ M solution in xylene; and (12C) HBC—$C_{12}$ structures casted from $10^{-4}$ M solution in toluene.
Figure 12B:
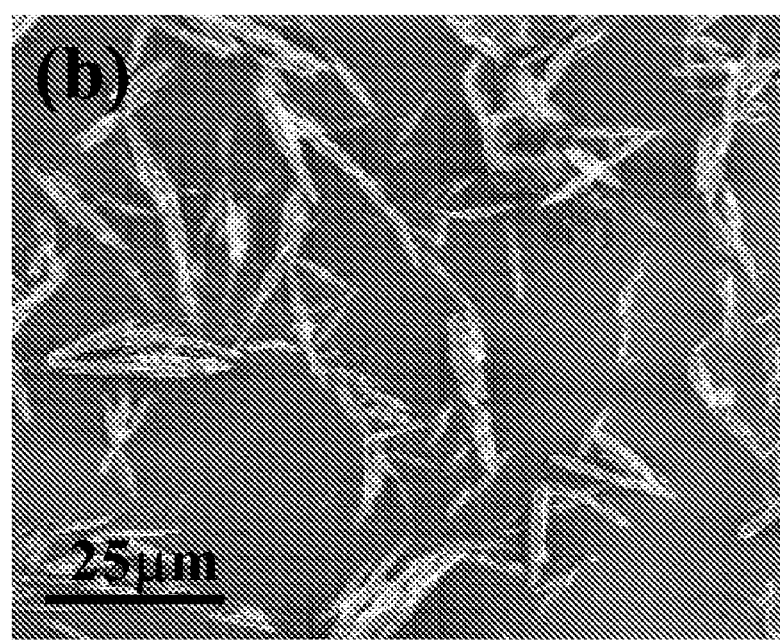
Figure 12C:
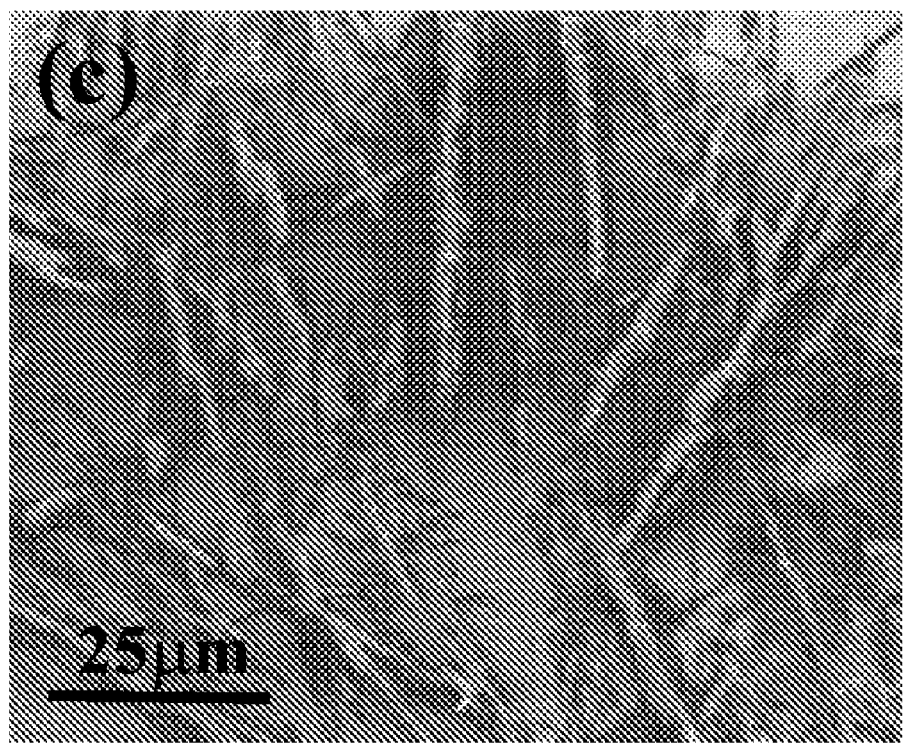

SWCNTs were then functionalized with two types of discotic hexa-peri-hexabenzocoronene (HBC) derivatives having different side groups. The HBC derivatives self-assemble to form large sponge-like structures. The synthesis of the HBC derivatives used in the current study has been described by Kastler et al. (*J. Am. Chem. Soc,* 2005, 127, 4286). Discrete, statistically distributed HBC micro-structures were formed on top of the random network of SWCNTs by drop casting 40 μl of either $10^{-3}$ M HBC—$C_{6,2}$ solution in xylene or $10^{-4}$ M HBC—$C_{12}$ solution in toluene (FIGS. 12B and 12C, respectively). The apparatuses were slowly dried under ambient conditions for half an hour to enhance the self-assembly of the HBC molecules. Then the apparatuses were annealed at 100° C. for 1 hour on a hot plate to evaporate the residual solvent.

The sensors were electrically tested during exposure to the analytes in a home-made setup containing an automated, computer-controlled flow system, capable of regulating the concentration of analytes via their vapor pressure, and an exposure chamber which can accommodate up to 10 apparatuses. In these experiments, the concentration of the analytes was kept constant at $p_a/p_o=1$, where $p_o$ is the partial pressure of the analytes and $P_o$ is the saturated vapor pressure.

An Agilent multifunction switch 34980 was used to subsequently address the apparatuses in the exposure chamber. A Stanford Research System SR830 DSP lock-in amplifier controlled by an IEEE 488 bus was used to supply the AC voltage signal (0.2V at 1 kHz) and measure the corresponding current, which was 10 μA. This setup allowed the measurement of normalized changes in conductance as small as 0.01%.

Example 15

Single-Walled Carbon Nanotubes Functionalized with Sponge-Like Structures of Hexa Peri-Hexabenzocoronenes Derivatives SWCNTs prepared according to Example 14 hereinabove, were functionalized with hexa-peri-hexabenzocoronenes (HBC) derivatives. The two HBC derivatives used in this study, HBC—$C_{12}$ and HBC—$C_{6,2}$, showed great variability in their aggregation behavior when casted from solution. In order to achieve comparable surface coverage of ~20% and ~40% for HBC—$C_{6,2}$ and HBC—$C_{12}$ layers, respectively, a $10^{-3}$ M HBC—$C_{6,2}$ solution in xylene and a $10^{-4}$ M HBC—$C_{12}$ solution in toluene were used (FIGS. 12B and 12C, respectively). The conducting HBC wires did not form a continuous network, resulting in no conducting paths which were formed within the layer. Electric conduction therefore occurred solely within the underlying CNT random network. Instead, the stacks of HBC molecules self-assembled into well-separated, micrometer size, sponge-like structures with large surface-to-volume ratios. The HBC—$C_{6,2}$ structures were about 20 μm long, 4 μm thick and covered approximately 20% of the surface. The HBC—$C_{12}$ structures were about 50 μm long, 1 pan thick and covered approximately 40% of the surface layers to form discontinuous and discrete sponge-like microstructures.

Example 16

Analyte Vapor Detection by Single-Walled Carbon Nanotubes Functionalized with Sponge-Like Structures of Hexa-Peri-Hexabenzocoronenes Derivatives The apparatuses prepared according to Examples 14 and 15 hereinabove, were tested for their response to various analyte biomarkers. Deionized-water (18.2 MΩ·cm; Easypure II), methanol, octane and decane (Sigma Aldrich Ltd. >98% purity) were used as the analytes. Octane and decane were used as non-polar (0 Debye) breath biomarkers of cancer and methanol was used as a more polar organic molecule.

The analytes were supplied via a flow system similar to the one connected to the exposure chamber for electrical testing.

Bare and functionalized random network of SWCNT chemiresistors were electrically tested upon exposure to the analytes. A supply of purified, dry air was split into two streams, one used as carrier gas and the other was directed through a bubbler containing the liquid analyte to generate saturated analyte vapor with $p_a/p_o=1$. The exposure chamber was exposed to the analyte for a time interval of 10 minutes followed by 10 minutes exposure to carrier gas flow. The exposure chamber was continuously flushed with the carrier gas to provide lower concentrations of analyte vapor. The sensor was alternatively exposed to the analyte and to dry air between 3 and 6 times during each test sequence. The response of the random network of SWCNT apparatuses to all four analytes was tested before functionalizing them with the HBC layers. Thereafter the apparatus was flushed for half an hour with dry air to clean the surface from any residual analytes. Quartz crystal microbalance (QCM) measurements of similar HBC/random network-SWCNT composites confirmed that the surface of the random network SWCNTs after gas exposure was cleaned. Then, the response of the HBC-functionalized random network of SWCNT sensor to the same analytes was tested and the results were compared.

Figure 13A:
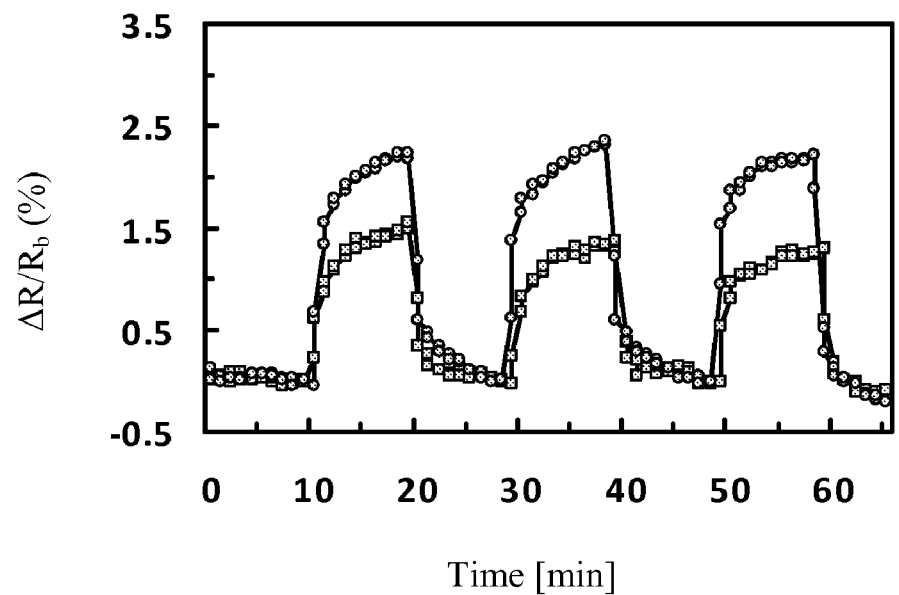
FIGS. 13A-13D are graphs of normalized resistance, $\Delta R/R_b$, of a random network SWCNT sensor prior to (squares) and after the functionalization with a discontinuous HBC—$C_{12}$ layer (circles) upon exposure to (13A) decane, (13B) octane, (13C) water and (13D) methanol in the vapor phase.
Figure 13B:
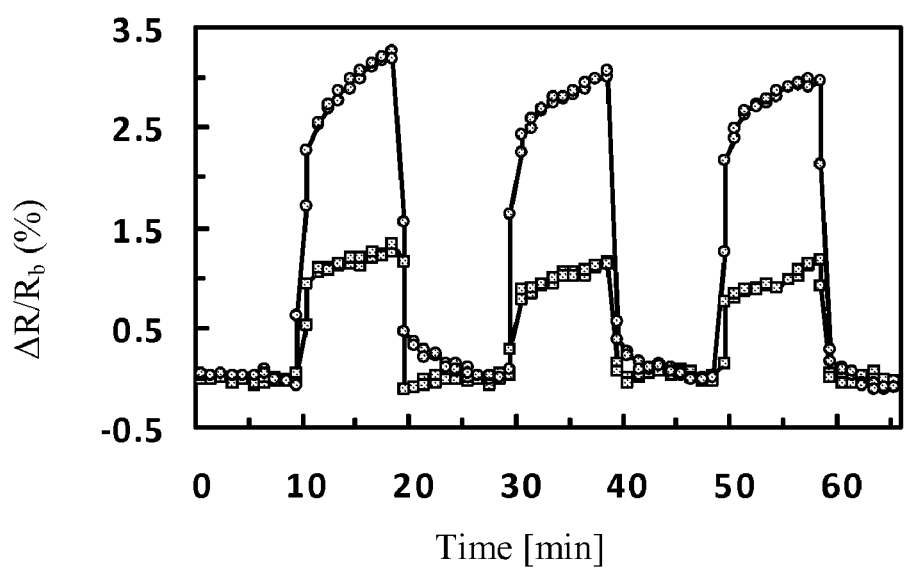
Figure 13C:
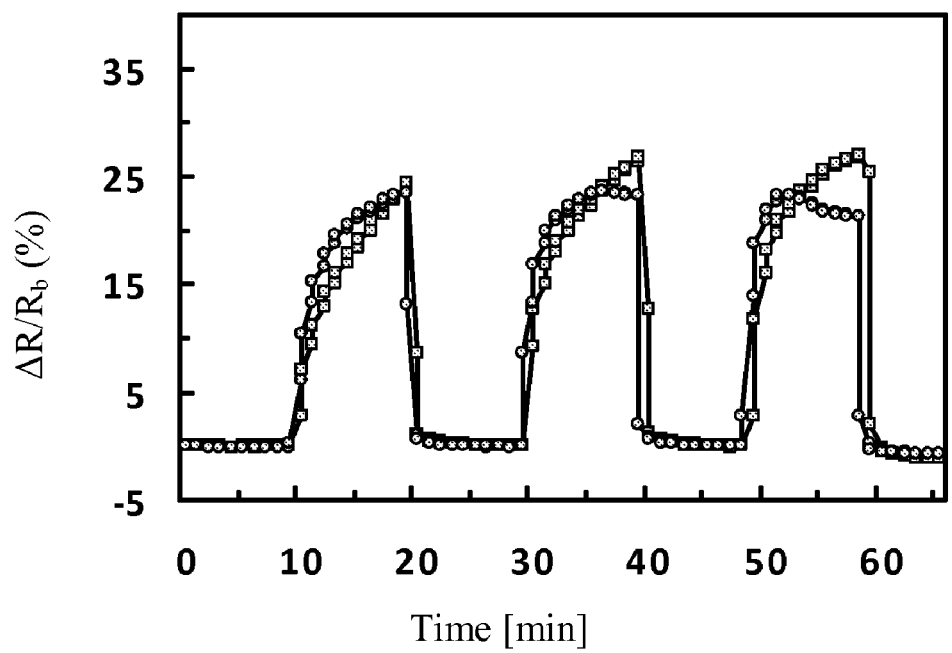
Figure 13D:
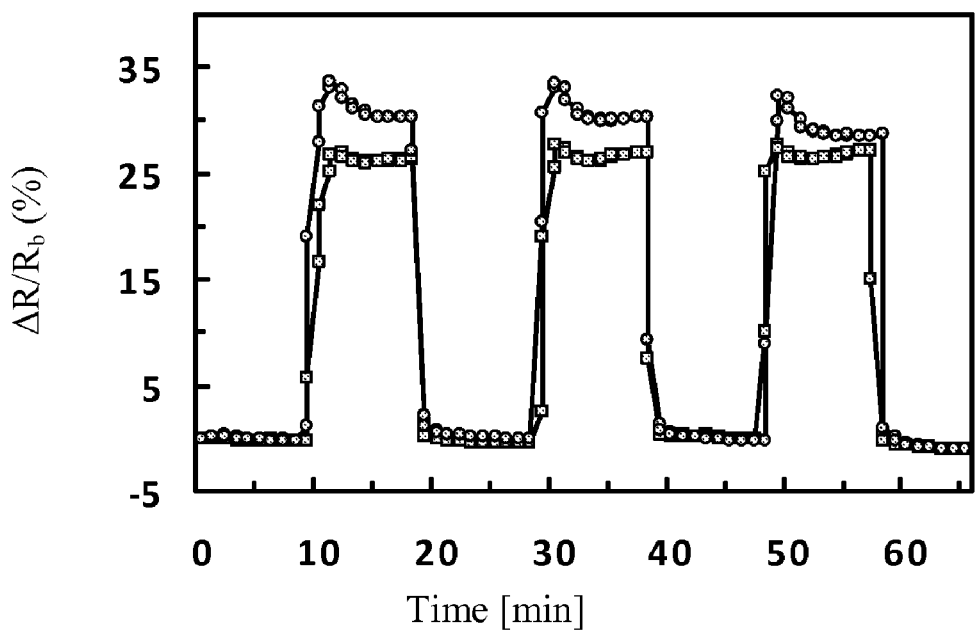
Figure 14A:
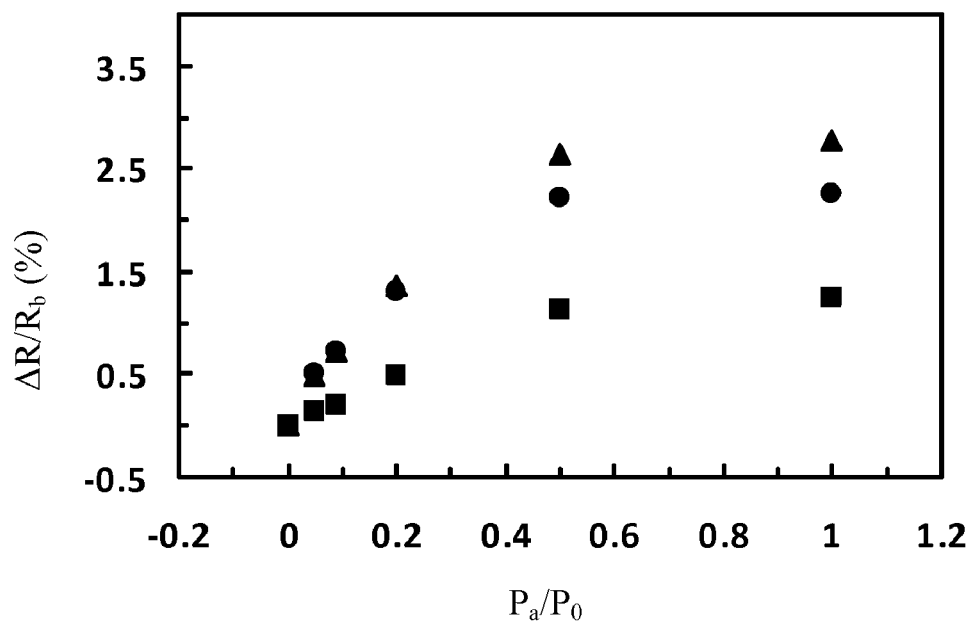
FIGS. 14A-14D are calibration curves: $\Delta R/R_b$ versus analyte concentration. The normalized resistance, $\Delta R/R_b$, of a random network SWCNT sensor before (squares) and after the functionalization with a discontinuous HBC—$C_{12}$ (circles) or HBC—$C_{6,2}$ (triangles) layers, upon exposure to (14A) decane, (14B) octane, (14C) water, and (14D) methanol in the vapor phase. All presented values of $\Delta R/R_b$ have signal-to-noise ratios larger than 3.
Figure 14B:
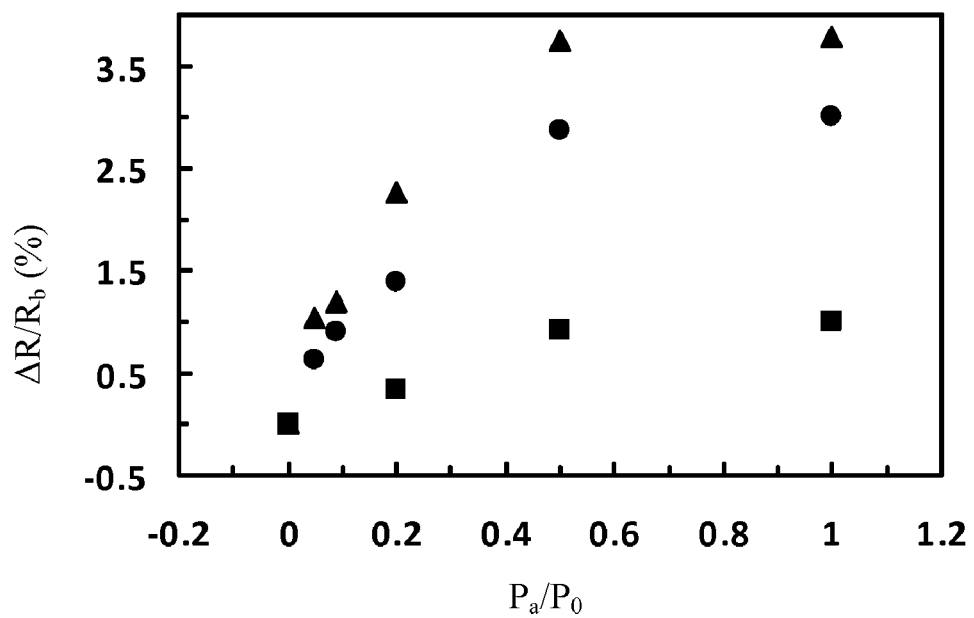
Figure 14C:
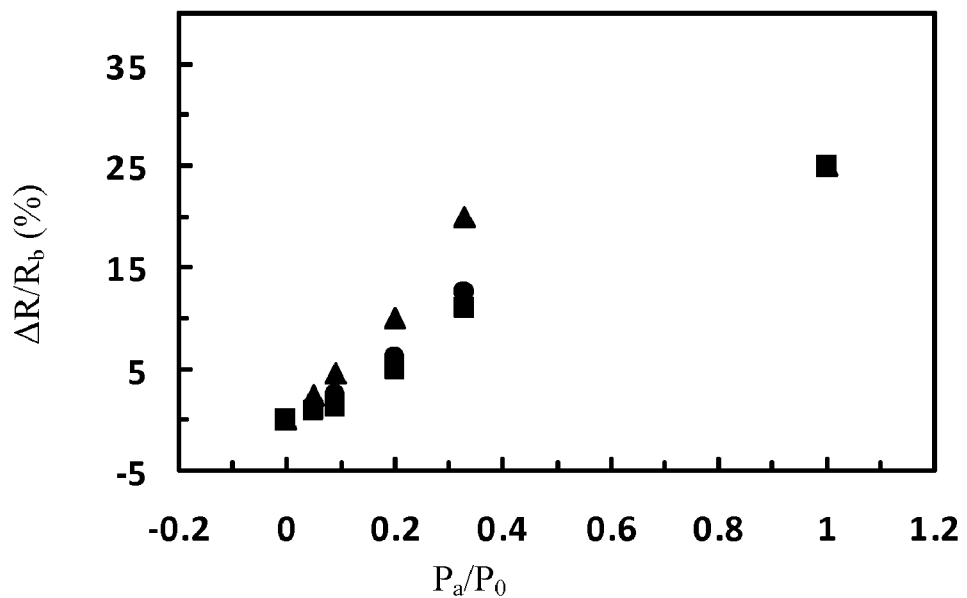
Figure 14D:
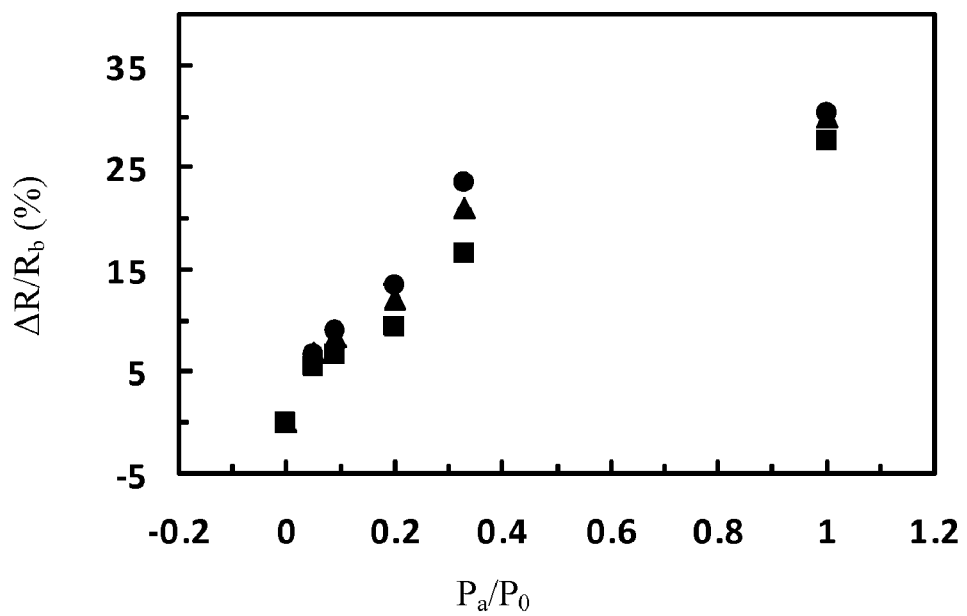

The morphology of the discontinuous HBC layers critically affected the sensing properties of the HBC-functionalized random network of SWCNT chemiresistors. FIGS. 13A-13D show the time dependence of the response, $\Delta R/R_b=(R-R_b)/R_b$ (R is the steady state resistance of the sensor when exposed to the analyte and $R_b$ is the baseline resistance when flushed with dry air, in the absence of the analyte) of a random network of SWCNT chemiresistor to pulses of decane (13A), octane (13B), water (13C) and methanol (13D), of bare and HBC—$C_{12}$ functionalized random network of SWCNTs. The time dependence of $R_b$ was interpolated by a linear fit and used to calculate the response shown in FIGS. 13A-13D. The response upon exposure to analyte vapors was rapid and fully reversible when flushed with dry air. The bare random network SWCNT sensors (squares) showed a large increase in the resistance of about 25% upon exposure to the polar analytes water and methanol (FIGS. 13C and 13D, respectively). The effect of the HBC functionalizaton on the conductance response to the polar analytes was almost negligible, where the responses to water of bare and functionalized sensors were essentially identical and the response to methanol increased by less than 10% after the functionalization with HBC—$C_{12}$.

The response of random network of bare SWCNTs to the non-polar VOCs was significantly smaller in comparison to the response to polar analytes. Exposure to decane and octane showed only minor responses, namely the resistance increased by 1.3% and 1.2%, respectively. Functionalization with HBC structures significantly affected the response to non-polar VOCs. The response increased by factors of 1.8 and 2.7 for decane and for octane, respectively. Hence, HBC—$C_{12}$ functionalization does not only lead to a larger response with improved signal-to-noise ratios, but also to improved selectivity, allowing the discrimination between different non-polar VOCs. Functionalization with HBC—$C_{6,2}$ structures provided additional improvement to the sensitivity and selectivity for non-polar VOCs, increasing the response to decane and octane by a factor of 2.0 and 3.4, respectively. FIGS. 14A-14D display the calibration curves, $\Delta R/R_b$ vs. analyte concentration ($p_a/p_o$ raging from 0.05 to 1) for a random network SWCNT sensor before (squares) and after functionalization with discontinuous HBC—$C_{12}$ (circles) or HBC—$C_{6,2}$ (triangles) layers. The enhanced signal of functionalized CNTs for non-polar analytes can be observed at all concentrations.

Figure 15:
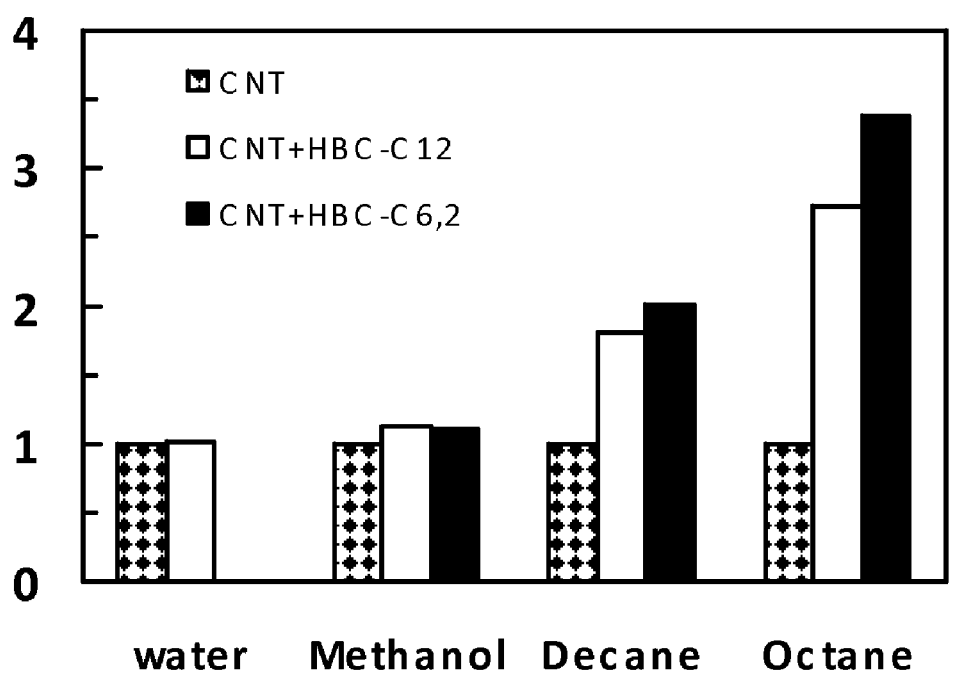
FIG. 15 is a diagram of the response of two kinds of HBC-functionalized random network SWCNT sensors, normalized to the response of the corresponding bare sensor, to water, methanol, decane and octane.

FIG. 15 shows the response of the HBC-functionalized sensors, normalized to the response of the corresponding bare sensor, to water, methanol, decane and octane. The improved sensitivity and selectivity to non-polar VOCs can clearly be observed.

Example 17

Analyte Vapor Detection by Single-Walled Carbon Nanotubes Functionalized with Sponge-Like Structures of Hexa-Peri-Hexabenzocoronenes Derivatives Via Spectroscopic Ellipsometry In order to confirm that the exposure to the non-polar VOCs causes swelling of the HBC-structures, the changes in average thickness of a discontinuous HBC—$C_{12}$ layer deposited directly on a Si/SiO$_2$ substrate after analyte exposure were monitored. The monitoring was performed after a 10 min exposure to water, decane and octane using spectroscopic ellipsometry. Discontinuous HBC layers were directly deposited on the Si/SiO$_2$ substrates, without the underlying 2D random network of SWCNT layer and the electrodes. The spectra were recorded over a range from 250-1700 nm at an incidence angle of 75°, using a spectroscopic phase modulated ellipsometer equipped with a specially designed triangular exposure cell.

The exact thickness of the SiO$_2$ layers was determined experimentally for every substrate prior to the deposition and functionalization of the random network SWCNT layers, using tabulated values for the refractive indices of Si and SiO$_2$ (Aspnes et al., *J. Electrochem. Soc.*, 1980, 127, 1359; Philipp, *Handbook of Optical Constants of Solids*, Palik Ed., Academic Press Inc., Orlando, Fla., 1985). A three-phase overlayer/SiO$_2$/Si model to extract an average thickness of the HBC layers was used. An area of about 1×5 mm² with local variations of the thickness were measured by spectroscopic ellipsometry. An increase in the average thickness upon exposure to the analyte vapors, measured at the same spot, was used to determine the amount of analytes adsorbed to the CNT mesh. A Cauchy dispersion of the refractive index for the HBC/random network-CNT composite layers was assumed. Bruggeman's effective medium approximation was further used to account for the inclusion of voids. Keeping the refractive index constant, thickness changes of 2±1 Å, 15±1 Å and 85±4 Å upon exposure to the vapors of water, decane and octane, respectively were extracted.

Measurements showed that repeated exposure to alternating flows of analyte vapor and carrier gas were reversible, though the baseline thickness increased slightly after each exposure to decane and octane, indicating that some residual swelling occurred. While water exposure showed little effect on the hydrophobic HBC structure, exposure to decane caused an increase in the thickness of the HBC layer indicating the swelling of the HBC agglomerates. Exposure to octane vapors of the same concentration resulted in a more pronounced increase in the thickness, indicating stronger swelling. Without being bound by any theory or mechanism of action, the swelling of the HBC structures in response to analyte exposure influences the conductance response of HBC functionalized random network SWCNT sensors. Clearly, HBC functionalized random network SWCNT sensors are capable of detecting and differentiating between non-polar biomarkers as well as between biomarkers which exhibit higher polarity. Most importantly, HBC functionalized random network SWCNTs sensors enable the detection of chemical and biological agents having small or negligible dipole moments including, in particular, many cancer biomarkers which have hitherto been difficult to trace.

Therefore, HBC-functionalized random network SWCNTs enable the detection of VOCs of varying polarities indicative of cancer. The structures of the HBC coating can be tailored by controlling the microstructure, surface coverage, distribution and chemical selectivity with suitable choice of side groups, concentration in solution and type of solvent, to provide a marked improvement of the sensitivity and selectivity of random networks of SWCNT chemiresistors, particularly to non-polar VOCs.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A system for detecting volatile organic compounds derived from a breath sample, the system comprising:
    (a) an apparatus comprising an array of chemically sensitive sensors of single walled carbon nanotubes coated with non-polymeric, non-polar small organic molecules, wherein the organic molecules comprise functional groups selected from the group consisting of alkyl, cycloalkyl, alkenyl, alkynyl, aryl, heterocyclyl, heteroaryl, alkylaryl, alkylalkenyl, alkylalkynyl, alkylcycloalkyl, alkylheterocyclyl, and alkylheteroaryl groups, and combinations thereof, wherein the functional groups are unsubstituted or substituted by at least one of a carboxyl, an acyl, an amido, an ester, a nitro, an azido, a halogen, a hydroxyl or a haloalkyl moiety; and
    (b) a processing unit comprising a learning and pattern recognition analyzer wherein the learning and pattern recognition analyzer receives sensor output signals from the apparatus and compares them to stored data.

2. The system according to claim 1 further comprising a breath collector, wherein the breath collector comprises at least one of a unit for concentrating breath analytes and a dehumidifying unit.

3. The system according to claim 1, wherein the single walled carbon nanotubes are organized in a random network configuration; or wherein the single walled carbon nanotubes have diameters ranging from about 0.9 nanometer to about 5 nanometers, and lengths ranging from about 1 micrometer to about 50 micrometers.

4. The system according to claim 1, wherein the non-polymeric, non-polar small organic molecules are selected from the group consisting of propyl gallate, anthracene, tetracosanoic acid, tricosane, 3-methyl-2-phenyl valeric acid, tris(hydroxymethyl)nitro-methane, tetracosane, dioctyl phthalate, 1,2,5,6,9,10-hexabromo-cyclododecane, pentadecane, hexa-peri-hexabenzocoronene (HBC) derivatives selected from the group consisting of HBC—$C_{6,2}$, HBC—$C_{10,6}$, HBC—$C_{14,10}$, HBC—$C_{12}$, and combinations thereof.

5. The system according to claim 1, wherein the sensors are configured in a form selected from the group consisting of capacitive sensors, resistive sensors, impedance sensors, and field effect transistor sensors.

6. The system according to claim 1, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (REF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

7. A method of determining at least one of the composition and concentration of volatile organic compounds in a breath sample, comprising the steps of:
    (a) providing a system according to claim 1,
    (b) exposing the sensor array of the apparatus to the sample, and
    (c) using pattern recognition algorithms to detect the presence of the volatile organic compounds in the sample.

8. The method according to claim 7 further comprising the step of collecting the sample into a breath collector prior to step (b), wherein the breath collector comprises at least one of a unit for concentrating breath analytes and a dehumidifying unit.

9. The method according to claim 7, wherein the single walled carbon nanotubes are organized in a random network configuration; or wherein the single walled carbon nanotubes have diameters ranging from about 0.9 nanometer to about 5 nanometers, and lengths ranging from about 1 micrometer to about 50 micrometers.

10. The method according to claim 7, wherein the non-polymeric, non-polar small organic molecules are selected from the group consisting of propyl gallate, anthracene, tetracosanoic acid, tricosane, 3-methyl-2-phenyl valeric acid, tris(hydroxymethyl)nitro-methane, tetracosane, dioctyl phthalate, 1,2,5,6,9,10-hexabromo-cyclododecane, pentadecane, hexa-peri-hexabenzocoronene (HBC) derivatives selected from the group consisting of HBC—$C_{6,2}$, HBC—$C_{10,6}$, HBC—$C_{14,10}$, HBC—$C_{12}$, and combinations thereof.

11. The method according to claim 7, wherein the sensors are configured in a form selected from the group consisting of capacitive sensors, resistive sensors, impedance sensors, and field effect transistor sensors.

12. The method according to claim 7, wherein the learning and pattern analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (REF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

13. A method for diagnosing a disease from a breath sample of a subject, comprising:
    (a) providing a system according to claim 1,
    (b) exposing the sensor array of the apparatus to the sample, and
    (c) using pattern recognition algorithms to detect volatile organic compounds in the sample indicative of a disease in the subject, thereby providing the diagnosis of said disease.

14. The method according to claim 13 further comprising the step of collecting the sample into a breath collector prior to step (b), wherein the breath collector comprises at least one of a unit for concentrating breath analytes and a dehumidifying unit.

15. The method according to claim 13, wherein the single walled carbon nanotubes are organized in a random network configuration; or wherein the single walled carbon nanotubes have diameters ranging from about 0.9 nanometer to about 5 nanometers, and lengths ranging from about 1 micrometer to about 50 micrometers.

16. The method according to claim 13, wherein the non-polymeric, non-polar small organic molecules are selected from the group consisting of propyl gallate, anthracene, tetracosanoic acid, tricosane, 3-methyl-2-phenyl valeric acid, tris(hydroxymethyl)nitro-methane, tetracosane, dioctyl phthalate, 1,2,5,6,9,10-hexabromo-cyclododecane, pentadecane, hexa-peri-hexabenzocoronene (HBC) derivatives selected from the group consisting of HBC—$C_{6,2}$, HBC—$C_{10,6}$, HBC—$C_{14,10}$, HBC—$C_{12}$, and combinations thereof.

17. The method according to claim 13, wherein the sensors are configured in a form selected from the group consisting of capacitive sensors, resistive sensors, impedance sensors, and field effect transistor sensors.

18. The method according to claim 13, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

19. The method according to claim 13, wherein the disease is selected from the group consisting of cancer, arthritis, arthritic conditions, atherosclerosis, kidney diseases, type 2 diabetes, chronic obstructive pulmonary disease (COPD), age related macula degeneration (AMD), neurodegenerative diseases, Alzheimer's disease, Parkinson's disease and amyotrophic lateral sclerosis (ALS).

20. The method according to claim 19, wherein the disease is cancer selected from the group consisting of lung cancer, prostate cancer, breast cancer, skin cancer, colon cancer, pancreatic cancer, lymphoma, leukemia, head and neck cancer, kidney cancer, ovarian cancer, bone cancer, liver cancer and thyroid cancer.

21. The system according to claim 1, wherein the functional groups are unsubstituted, or substituted with at least one of a carboxyl, an acyl, an ester, a nitro, a halogen, or a haloalkyl moiety.

22. The system according to claim 1, wherein exposure of said apparatus to human breath comprising volatile organic compounds (VOCs) results, for one or more sensors of said array, in a measurable change in one or more of conductivity, resistance, independence, capacitance, inductance, or an optical property of said sensors on exposure of the sensors to said VOCs.

* * * * *